(12) United States Patent
Choi

(10) Patent No.: US 11,903,721 B1
(45) Date of Patent: Feb. 20, 2024

(54) DIGITAL APPARATUS AND APPLICATION FOR TREATING MILD COGNITIVE IMPAIRMENT AND DEMENTIA

(71) Applicant: S-Alpha Therapeutics, Inc., Seoul (KR)

(72) Inventor: Seung Eun Choi, Seoul (KR)

(*) Notice: Subject to any disclaimer, the term of this patent is extended or adjusted under 35 U.S.C. 154(b) by 0 days.

(21) Appl. No.: 18/082,722

(22) Filed: Dec. 16, 2022

Related U.S. Application Data

(63) Continuation of application No. 16/860,641, filed on Apr. 28, 2020, now abandoned.

(51) Int. Cl.
*A61B 5/00* (2006.01)

(52) U.S. Cl.
CPC .......... *A61B 5/4088* (2013.01); *A61B 5/7465* (2013.01)

(58) Field of Classification Search
CPC ... A61B 5/4088; A61B 5/4064; A61B 5/4076; A61B 5/7465; A61N 1/36025; A61N 1/36082
See application file for complete search history.

(56) References Cited

U.S. PATENT DOCUMENTS

| | | | |
|---|---|---|---|
| 6,527,712 | B1 | 3/2003 | Brown et al. |
| 10,559,221 | B2 | 2/2020 | Martucci et al. |
| 2003/0135095 | A1 | 7/2003 | Iliff |
| 2006/0183980 | A1 | 8/2006 | Yang |
| 2006/0189885 | A1 | 8/2006 | Yelland et al. |
| 2006/0292531 | A1 | 12/2006 | Gibson |
| 2008/0086318 | A1 | 4/2008 | Gilley et al. |
| 2015/0161330 | A1 | 6/2015 | Joao et al. |
| 2016/0321945 | A1* | 11/2016 | DenBoer ................ G09B 19/00 |
| 2017/0098385 | A1 | 4/2017 | Martucci et al. |
| 2018/0177973 | A1 | 6/2018 | Keene et al. |

(Continued)

FOREIGN PATENT DOCUMENTS

| | | |
|---|---|---|
| JP | 2017-518856 A | 7/2017 |
| KR | 10-2005-0054379 A | 6/2005 |

(Continued)

OTHER PUBLICATIONS

International Search Report and Written Opinion issued in related International Patent Application No. PCT/KR2022/009557 dated Oct. 7, 2022.

*Primary Examiner* — Scott M. Getzow
(74) *Attorney, Agent, or Firm* — Morgan, Lewis & Bockius LLP

(57) ABSTRACT

Methods and apparatuses are described herein for treating a patient with mild cognitive impairment (MCI) or dementia by one or more digital therapeutics. For example, a patient who has been diagnosed with the MCI or dementia may administer one or more digital therapeutics to the patient to improve a plurality of neurohumoral factors that cause the MCI or the dementia of the patient. The digital therapeutics may include one or more digital instructions that are generated to treat at least one imbalance of the plurality of neurohumoral factors based on at least one neurohumoral change among the plurality of neurohumoral factors by the patient's performance of the one or more digital instructions. The one or more digital instructions may include at least one of an execution environment setting, a lifestyle change, learning, exercising, or affirmation/achievement task.

23 Claims, 18 Drawing Sheets

(56) References Cited

U.S. PATENT DOCUMENTS

| | | | |
|---|---|---|---|
| 2018/0292888 A1* | 10/2018 | Slepian | A61B 5/4836 |
| 2019/0019581 A1 | 1/2019 | Vaughan et al. | |
| 2020/0261013 A1 | 8/2020 | Ben-Oren | |
| 2021/0201689 A1 | 7/2021 | Choi | |

FOREIGN PATENT DOCUMENTS

| | | |
|---|---|---|
| KR | 10-2013-0029284 A | 3/2013 |
| KR | 10-2013-0087075 A | 8/2013 |
| KR | 10-2017-0047942 A | 5/2017 |
| KR | 10-2018-0084332 A | 7/2018 |
| KR | 10-2019-0043107 A | 4/2019 |
| KR | 10-2020-0102718 A | 9/2020 |
| KR | 10-2021-0086246 A | 7/2021 |

* cited by examiner

| Execution environment setting ||
|---|---|
| Task | Execution |
| • Brightness<br>• Coziness<br>• Comport | • Record level of illumination, IoT lighting<br>• Application environment setting<br>• Place setting – execution space |

FIG. 7A

| Lifestyle ||
|---|---|
| Task | Task |
| • New experience, travel<br>• Sex hormone balance recovery | • Daily journal<br>• Recording<br>• Diet record<br>• Nutrition evaluation |

FIG. 7B

| Memory/Learning | |
|---|---|
| Task | Execution |
| • Recollection learning<br>• Memory recognition treatment | • Play<br>• Participation log book |

FIG. 7C

| Exercise | |
|---|---|
| Task | Task |
| • Short term acute exercise (e.g., 20 min) | • Exercise daily record<br>• Heart rate (HR)<br>• Personal training coaching |

FIG. 7D

| Positive/Achievement ||
|---|---|
| Task | Execution |
| • Positive feeling<br>• Project<br>• Voluntary DTx participation | • Self-feedback & self-reward<br>• Rewards from patient-doctor relationship |

DIGITAL APPARATUS AND APPLICATION FOR TREATING MILD COGNITIVE IMPAIRMENT AND DEMENTIA

CROSS-REFERENCE TO RELATED APPLICATIONS

This application claims the benefit of Korean Application No. 10-2019-0180050, filed Dec. 31, 2019, the contents of which are incorporated herein by reference.

FIELD OF INVENTION

The disclosed embodiments are generally related to digital therapeutics (DTx) and more specifically, to inhibition of progression and treatment of amnestic mild cognitive impairment (MCI) and Alzheimer's disease (AD).

BACKGROUND

Dementia refers to a clinical syndrome that disables a person's ability to perform everyday activities due to postnatal cognitive decline in memories, languages, judgments, etc. Types of dementia are divided into degenerative dementia which includes Alzheimer's disease (AD), vascular dementia caused due to stroke, and others caused due to various factors such as injuries or drugs. Currently, U.S. Food and Drug Administration (FDA) approves two types of drugs for AD treatment: cholinesterase inhibitors (e.g., Donepezil, Rivastigmine and Galantamine) and N-methyl-D-aspartate (NMDA) antagonist (e.g., Memantine). However, the therapeutic effect of these drugs is highly limited. Specifically, the aforementioned drugs only serve to ease the symptoms rather than halt disease's progression or cure the disease itself. In addition, the questions of the uselessness of drug treatment for dementia have been raised as drug treatment often entails serious fatal side effects. Furthermore, the fact that there are too many interactions between drugs may be dangerous to patients who take such drugs. Thus, methods and apparatuses that, can treat or inhibit the progression of amnestic MCI and AD without such limitations are needed.

SUMMARY

Methods and apparatuses are described herein for treating a patient with mild cognitive impairment (MCI) or dementia by one or more digital therapeutics. For example, a medical profession (e.g., a doctor) may determine whether the patient has the MCI or the dementia based on one or more symptoms of the MCI or the dementia. If the patient has been diagnosed with the MCI or the dementia, the medical professional may prescribe and/or administer the one or more digital therapeutics to the patient to improve a plurality of neurohumoral factors that cause the MCI or the dementia. The one or more digital therapeutics comprise one or more digital instructions that are generated to treat at least one imbalance of the plurality of neurohumoral factors based on at least one neurohumoral change among the plurality of neurohumoral factors by the patient's performance of the one or more digital instructions. The plurality of neurohumoral factors may include at least one of sex steroid hormone, insulin-like growth factor-2 (IGF-2), β-catenin in Wnt signaling, Bcl-2—associated athanogene 1 (BAG1), cAMP response element-binding protein (CREB), inflammation factors, corticosteroids, or neurohormones. The at least. one imbalance of the plurality of neurohumoral factors includes at least one of a sex steroid hormone imbalance, a IGF-2 decrease, a β-catenin degradation, a BAG1 inactivation, a CREB inactivation, an increase in inflammation factors, a corticosteroids increase, or a neurohormone decrease. The one or more digital therapeutics is performed by a user's device.

BRIEF DESCRIPTION OF THE DRAWINGS

A more detailed understanding may be had from the following description, given by way of example in conjunction with the accompanying drawings, wherein like reference numerals in the figures indicate like elements, and wherein:

FIG. 7A is a diagram illustrating an example digital instruction for an execution environment setting;

FIG. 7B is a diagram illustrating an example digital instruction for a lifestyle module;

FIG. 7C is a diagram illustrating an example digital instruction for a memory/learning module;

FIG. 7D is a diagram illustrating an example digital instruction for an exercise module;

FIG. 7E is a diagram illustrating an example digital instruction for a positive/achievement module;

DETAILED DESCRIPTION

Figure 1A:
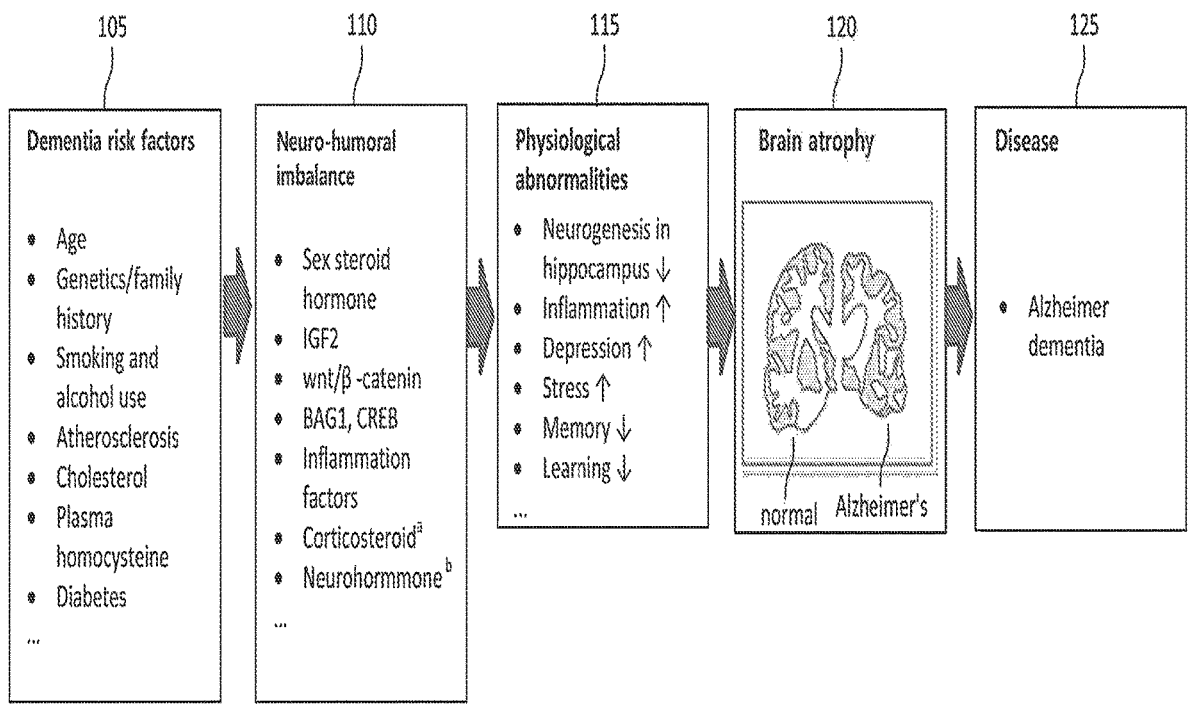
FIG. 1A is a system diagram illustrating an example mechanism of action (MOA) of Alzheimer's disease (AD)

According to "Year 2016 nationwide dementia epidemiology survey"(Report Number: NDR-1603-0015, 2017, Jun., Central Dementia Center, Ministry of Health and Welfare, Korea, Republic of.), the standardized dementia prevalence rate of male Korean elderly among aged 65 or older was 8.18% and that of the female was 10.46%, making a total of 9.50%. The data shows that women's prevalence rate was higher than that of men.

Further specifying the types of dementia from the standardized dementia prevalence rate among Korean elderly aged 65 or older(9.50%), AD counted for 7.07% of the total, while vascular dementia counted for 0.83% and the others for 1.60%. It is clear that AD takes an overwhelmingly large proportion (approximately 3/4) when compared to the other types of dementia.

What is noticeable is the increase in the standardized dementia prevalence rate along with population ageing. Comparing the standardized prevalence rate of Korean elderly aged 65 or older with that of the Korean elderly aged 85 or older, the rate goes up from 9.50% to 38.39%. The standardized dementia prevalence rate of men aged 85 or older, in particular, rises to 53.99%.

The dementia prevalence rate of Korean elderly and the number of dementia patients estimated with the future population based on the data concerning age, sex and region standardization of 2015 population census is even more noticeable. The standardized dementia prevalence rate among those aged 65 or older in 2016 of 9.73% is estimated to rise as 10.29% in 2020, 10.56% in 2030, and 16.09% in 2050. According to the estimated shift, the number of Korean dementia patients by 2025 is over 1 million, and by 2050 over 3 million.

MCI(Korean Standard Disease and Sign Classification Code: F06.7), as an intermediate state between normal aging and dementia, does not cause any difficulty in everyday activities but results in a decline of memories and cognitive functions compared to a person's age group. Types of MCI are divided into amnestic MCI which entails memory loss and non-amnestic MCI which causes a decline of non-memory-related cognitive functions. As it is known that about half of MCI develops into dementia, MCI, in terms of preventing dementia, is receiving attention from the public.

According to the aforementioned report, the standardized MCI prevalence rate for male Korean elderly aged 65 or older is 18.09%, and that of the female was 25.28%, making a total of 22.25%. The data shows that, as have been observed from the dementia prevalence rate, the female prevalence rate among those aged 65 or older was higher than that of men.

Further specifying the types of MCI from the standardized MCI prevalence rate among Korean elderly aged 65 or older(22.25%), amnestic MCI counted for 16.69% while non-amnestic MCI counted for 5.56%. Amnestic MCI takes about 3/4 of the total proportion. Amnestic MCI particularly requires a more active care as it has higher risks to be developed as dementia although it may not cause any difficulty in everyday lives.

Concerning the increase in the prevalence rate, dementia care cost per patient and government budget on dementia care should be noted. According to Korean Dementia Observatory 2018, Central Dementia Center, dementia care cost per patient is 20.74 million KRW and the government budget allocated for dementia care is 14.6 trillion KRW, which accounts for 0.8% of national GDP. Social costs of dementia is estimated to increase sharply from total investment 17.9 trillion KRW in 2020 to 87.2 trillion KRW in 2050, Korea, Republic of.

The increase in both the dementia prevalence rate and the government budget on dementia care is a global issue that many countries encounter although the specifics may vary depending on regions and progressions of population ageing.

In case of a vascular dementia patient, he or she may be cured by performing surgeries if the cause of dementia is due to stroke, brain tumor or normal pressure hydrocephalus (NPH). If it is the case of vascular dementia caused due to brain infraction, the patient may prevent the disease or delay its progression by eliminating or managing elements such as hypertension, diabetes, smoking, hyperlipidemia, etc. However, it is hard to expect a positive therapeutic effect with the aforementioned methods from an AD, which is degenerative dementia, patient unlike those with vascular dementia.

Currently, U.S. FDA approves two types of drugs for AD treatment: cholinesterase inhibitors such as Donepezil, Rivastigmine and Galantamine, and N-methyl-D-aspartate (NMDA) antagonist such as Memantine. Donepezil, which is cholinesterase inhibitor, is generally prescribed to treat all stages of AD, and Rivastigmine and Galantamine to treat mild to moderate stage of AD. Memantine in combination with Donepezil is prescribed to treat, moderate to severe stage of AD. However, the therapeutic effect of such drug treatment is highly limited. The aforementioned drugs only serve to ease the symptoms rather than halt disease's progression or cure the disease itself. At the same time, the questions of the uselessness of drug treatment for dementia have been raised as drug treatment entails serious and often fatal side effects and the fact that too many interactions between drugs may be dangerous has been pointed out. In fact, in France, insurance plans have suspended to cover the aforementioned four types of dementia treatment since Aug. 2018.

In addition, various cases where multinational pharmaceutical companies fail to develop or stop developing cure for AD (e.g., Fizer's Bapineuzumab, Eli Lilly and Company's Solanezumab, Merck's Verubecestat which is β-secretase(BACE) inhibitor, Boehringer Ingelheim's 'BI 409306', Astrazeneca's Saracatinib, Biogen's Aducanumab, Novartis and Amgen's 'CNP520 (Umibecestat)', Roche's Crenezumab) simply demonstrate the difficulty of developing AD treatment. Hence, it is predicted that no innovative AD treatment will emerge in near future.

In this disclosure, a digital apparatus and an application for inhibiting progression of and treating amnestic MCI and AD are provided based on mechanism of action (MOA) of amnestic MCI and AD, therapeutic hypothesis and digital therapeutic hypothesis for treating and/or inhibiting progression of MCI and AD.

Embodiments disclosed herein may be based on a rational design of the application in order for clinically yen Ting the digital therapeutic hypothesis for amnestic MCI and AD and embodying the digital therapy.

The MOA, therapeutic hypothesis and digital therapeutic hypothesis may be deduced based on neuro-humoral factors of amnestic MCI and AD. Based on the digital therapeutic hypothesis for amnestic MCI and AD, a credible digital apparatus and an application which inhibits progression of amnestic MCI and AD and offers improved therapeutic effect through patients' repetitive execution of digital instructions may be provided.

The digital apparatus for MCI and AD treatment in accordance with one embodiment may include a processor generating digital instructions. For example the processor generates a DTx module for MCI and AD treatment bases upon the MOA and therapeutic hypothesis of MCI and AD. The processor may further generate specified digital instructions based on the DTx module, and provide the aforementioned instructions to a first user, and the first user's execution outcomes of the digital instructions may be collected using the apparatus.

The digital application for MCI and AD treatment in accordance with one embodiment, as a digital application stored in a computer-readable medium, may instruct a computing apparatus to execute operations, which comprises: generating a DTx module for treating MCI and AD based on the MOA and therapeutic hypothesis of MCI and AD; generating specified digital instructions based on the DTx module; providing the digital instructions to a first user; and collecting the first user's execution outcomes of the digital instructions.

As described above, MOA, therapeutic hypothesis and digital therapeutic hypothesis may be obtained based on neuro-humoral factors of the progression of amnestic MCI and AD. Patients may be given digital tasks based on these findings, and their execution and completion of tasks may be collected and analyzed in order to effectively inhibit the progression of amnestic MCI and AD and offer improved therapeutic effect.

The development of new drugs starts with confirming a medical demand in situ, proposing a MOA based on the expert reviews and meta-analysis on the corresponding disease, and deducing therapeutic hypothesis based on the expert reviews and the meta-analysis. Also, after a library of drugs whose therapeutic effects are expected is prepared based on the therapeutic hypothesis, a candidate material is found through screening, and the corresponding candidate material is subjected to optimization and preclinical trials to check its effectiveness and safety from a preclinical stage, thereby deciding the candidate material as a final candidate drug. To mass-produce the corresponding candidate drug, a chemistry, manufacturing, and control (CMC) process is also established, a clinical trial is carried out on the corresponding candidate drug to verify a MOA and therapeutic hypothesis of the candidate drug, thereby ensuring the clinical effectiveness and safety of the candidate drug.

Drug targeting and signaling, which fall upstream of the development of new drugs, have many uncertainties. In many cases, because the drug targeting and signaling take a methodology of putting together the outcomes, which have been reported in the art, and interpreting the outcomes, it may be difficult to guarantee the novelty of invention. On the contrary, the invention of drugs capable of regulating the drug targeting and signaling to treat a disease requires the highest level of creativity except for the field of some antibody or nucleic acid (DNA, RNA) therapeutics in spite of the development of research methodology for research and development of numerous new drugs. As a result, the molecular structures of the drugs are the most critical factors in the field of new drugs.

Unlike the drugs, DTx are basically realized using a device that implements DTx. Due to the nature of the DTx, the rational design of DTx against the corresponding disease, and the realization of the DTx based on the rational design may be considered to be a very creative process when considering the clinical verification and approval processes as the therapeutics. That is, the core of the DTx depends on the rational design of DTx suitable for treatment of the corresponding disease, and the development of specific procedures capable of clinically verifying the DTx based on the rational design.

Figure 1B:
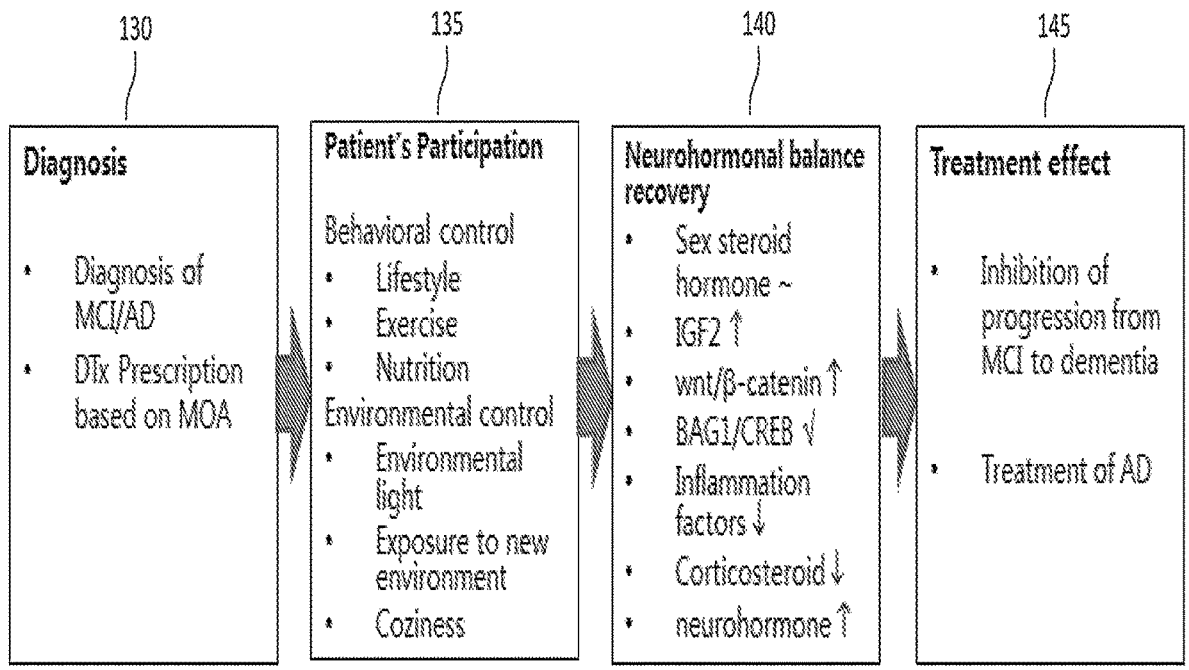
FIG. 1B is a system diagram illustrating an example treatment procedure based on therapeutic hypothesis for treating or inhibiting progression of MCI and AD.
Figure 1C:
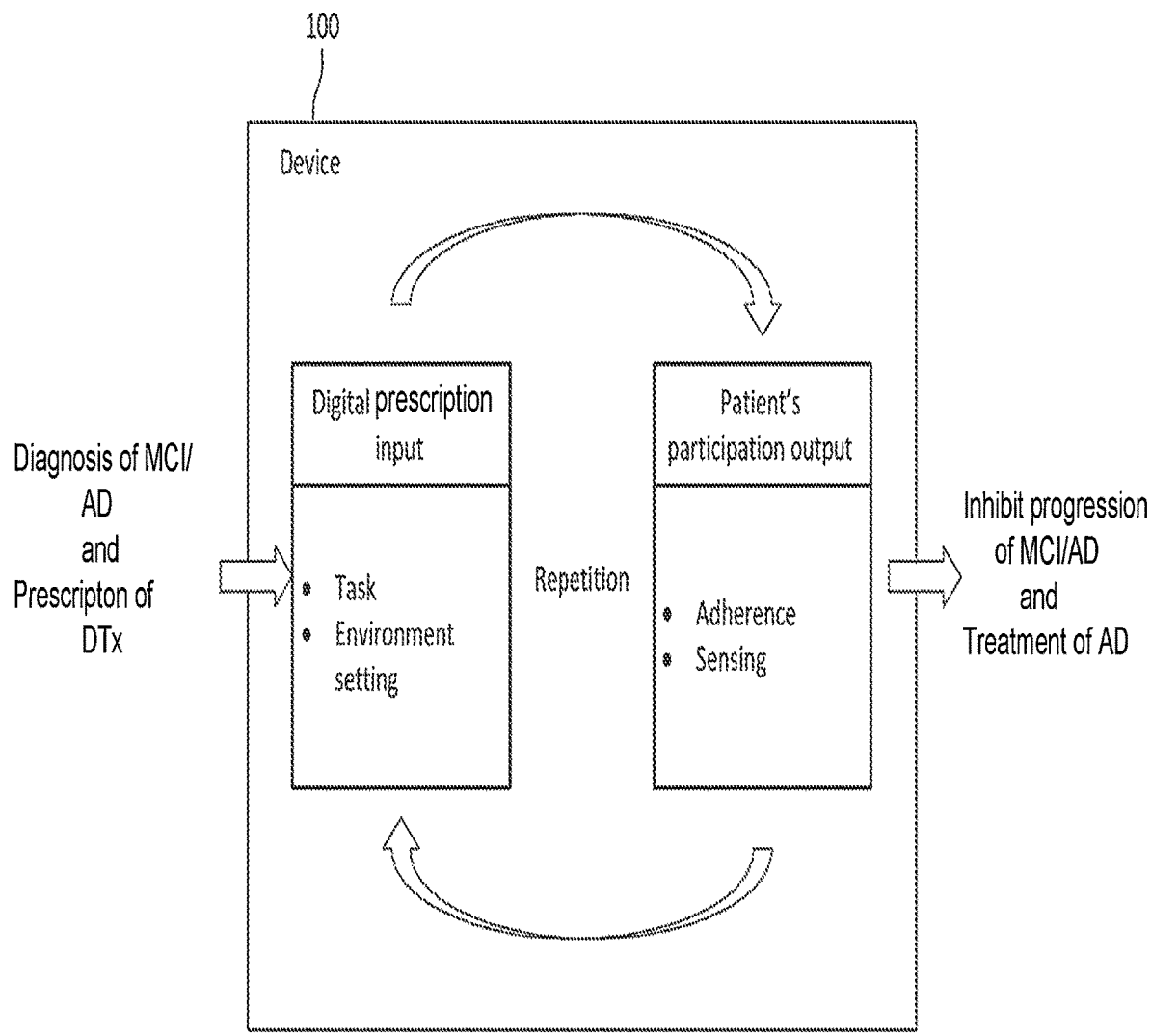
FIG. 1C is a system diagram illustrating another example treatment procedure based on a user device for treating or inhibiting progression of MCI and AD.

FIG. 1A illustrates an example mechanism of action (MOA) of Alzheimer's disease (AD), which may be used in combination with any of other embodiments described herein. FIG. 1B illustrates an example treatment procedure based on therapeutic hypothesis for treating or inhibiting progression of MCI and AD, which may be used in combination with any of other embodiments described herein. FIG. 1C illustrates another example treatment procedure based on a user device for treating or inhibiting progression of MCI and AD, which may be used in combination with any of other embodiments described herein.

A digital apparatus and an application for inhibiting progression of and treating MCI and AD may be realized based on the MOA and therapeutic hypothesis deduced through the literature search and expert reviews of clinical trial articles on amnestic MCI and AD.

Generally speaking, disease therapy is carried out by analyzing a certain disease in terms of pathophysiological functions and dispositions in order to determine a start point, a progression point, and an end point for the disease. Also, an indication of the disease is defined by characterization of the corresponding disease and statistical analysis of the disease. Also, patient's physiological factors, especially neuro-humoral factors, which correspond to the verified indications, are analyzed, and the patient's neuro-humoral factors are restricted to a narrow extent associated with the disease to deduce a MOA.

Next, therapeutic hypothesis, in which the corresponding disease is treated by controlling actions and environments directly associated with regulation of the corresponding neuro-humoral factors associated with the disease, is deduced. To realize this therapeutic hypothesis into digital therapeutics, digital therapeutic hypothesis for achieving a therapeutic effect through repeated digital instruction and execution, which are associated with the control of patient's action/environment regulation of neurohumoral factors, is proposed. The digital therapeutic hypothesis can be realized as a digital apparatus and an application configured to present changes in patient's actions (including behavioral, emotional, and cognitive areas), improvement of patient's environment, and patient's participation in the form of specific instructions and collect and analyze execution of the specific instructions.

The literature search for the clinical trials as described above may be executed through meta-analysis and data mining, and the clinical specialist's feedbacks and deep reviews may be applied in each analysis step. Basically, embodiments described herein encompasses extracting a MOA and therapeutic hypothesis for MCI and AD using the procedure as described above, and regulating the neuro-humoral factors based on these results to provide a digital apparatus and an application as DTx for inhibiting progression of and treating MCI and AD.

However, a method of extracting a MOA and therapeutic hypothesis for MCI and AD is not limited to the methods as described above, and MOAs and therapeutic hypotheses for diseases may be extracted using various methods.

Referring to FIG. 1A, various risk factors 105 in aging process such as age, inheritance/family history, smoking & drinking, arteriosclerosis, cholesterol, serum homocysteine, diabetes, MCI and other factors may cause the imbalance of neurohumoral factors in the aging process. For example, neuro-humoral factors 110, which may include abnormality in sex steroid hormone, decline in insulin-like growth factor-2 (IGF-2), abnormality in wnt/β-catenin, decline in BAG1, cAMP response element-binding protein (CREB), hypersecretion of corticosteroids such as inflammation factors, cortisol and glucocorticoid, and hyposecretion of neurohormones such as dopamine, noradrenaline and somatostatin, inhibit neurogenesis in hippocampus in terms of physiological functions, may cause inflammation in brain tissue, and can also cause stress and depression. These physiological abnormalities 115 or physiological factors, over a long period of time, may induce plaque deposits, and neuronal apoptosis, leading to brain atrophy 120 with plaque deposits as a result, which is the anatomical characteristics of AD. As a result, a clinical syndrome or disease 125 commonly referred to as dementia occurs, which entails malfunctioning of brain, decline in cognitive functions such as memory, language and judgment, and hence the difficulties in performing everyday life activities.

Referring to FIG. 1B, the therapeutic hypothesis for MCI and AD relates to inhibition of progression of and treatment of MCI and AD by restoring the balance of neuro-humoral factors 140 through patients' participation 135 including the patients' behavioral control (e.g., lifestyle, habits, exercise, sand nutrition) and environmental control (e.g., bright, familiar, relaxing execution atmosphere setting) after diagnosis 130 of MCI and/or AD. Restoring the balance of neuro-humoral factors 140 may result in treatment effect 145 in MCI and/or AD.

Referring to FIG. 1C, the digital therapeutic hypothesis for MCI and AD may be realized by a device 100 configured to present changes in patients' actions, improvement of patients' environment, and patients' participation in the form of specific instructions, and collect/analyze execution of the specific instructions. When the DTx are used, the imbalance of neuro-humoral factors for amnestic MCI and AD patients may be corrected through the digital inputs (instructions) and outputs (execution) to achieve inhibition of progression of and treatment of MCI and AD.

The MOA and the therapeutic hypothesis for MCI and AD described with reference to FIGS. 1A and 1B are not limited thereto. The methodology may be applied to other types of MCI and AD.

Also, although sex steroid hormone, IGF-2, wnt/β-catenin, BAG1, CREB, inflammation factors, corticosteroids and neurohormones are described as the neuro-humoral factors as shown in FIGS. 1A and 1B, it should be noted that the description of the neuro-humoral factors is given by way of illustration only, and are not intended to be limiting in all aspects of the MOA and the therapeutic hypothesis for amnestic MCI and AD.

Figure 2:
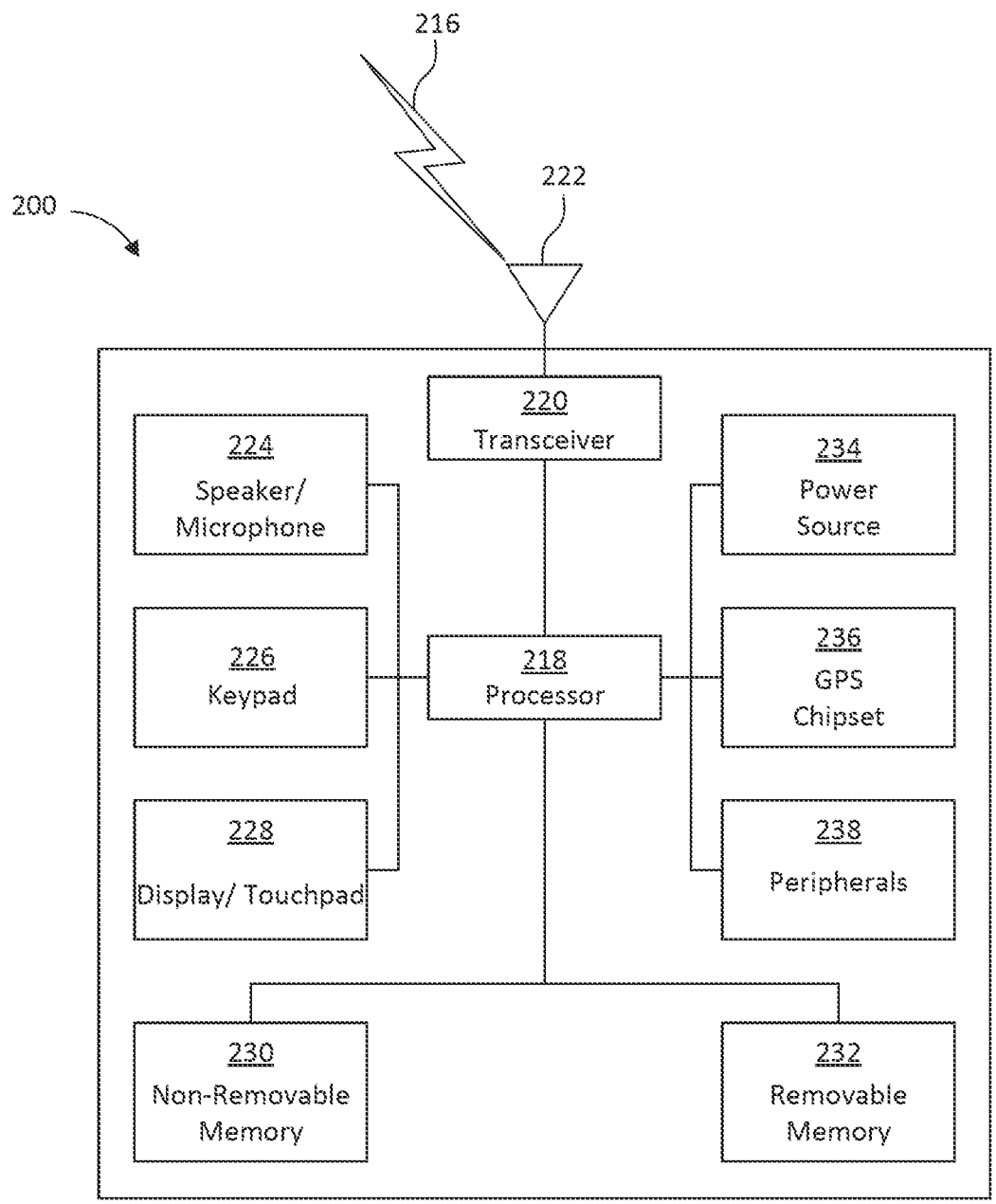
FIG. 2 is a diagram illustrating an example device that can be used to treat MCI and AD.

FIG. 2 is a system diagram illustrating an example device 200 that can be used for inhibiting progression of and treating amnestic MCI and AD, which may be used in combination with any of other embodiments described herein. As shown in FIG. 2, the device 200 may include a processor 218, a transceiver 220, a transmit/receive element 222, a speaker/microphone 224, a keypad 226, a display/touchpad 228, non-removable memory 230, removable memory 232, a power source 234, a global positioning system (GPS) chipset 236, and/or other peripherals 238, among others. It will be appreciated that the device 200 may include any sub-combination of the foregoing elements while remaining consistent with an embodiment. By way of example, the device 200 may include a mobile device, a user equipment (UE), a mobile station, a fixed or mobile subscriber unit, a subscription-based unit, a pager, a cellular telephone, a personal digital assistant (PDA), a smartphone, a laptop, a netbook, a personal computer, a wireless sensor, a hotspot or Mi-Fi device, an Internet of Things (IoT) device, a watch or other wearable, a head-mounted display (HMD), a vehicle, a drone, a medical device and applications (e.g., remote surgery), an industrial device and applications (e.g., a robot and/or other wireless devices operating in an industrial and/or an automated processing chain contexts), a consumer electronics device, a device operating on commercial and/or industrial wireless networks, and the like.

The processor 218 may be a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs), any other type of integrated circuit (IC), a state machine, and the like. The processor 218 may perform data processing, power control, input/output processing, sensor date processing, and/or any other functionality that enables the device 200 to treat mild cognitive impairment and dementia. The processor 218 may be coupled to the transceiver 220, which may be coupled to the transmit/receive, element 222. While FIG. 2 depicts the processor 218 and the transceiver 220 as separate components, it will be appreciated that the processor 218 and the transceiver 220 may be integrated together in an electronic package or chip.

The transmit/receive element 222 may be configured to transmit data to, or receive data from a sever located in a medical institution. For example, medical instructions from a doctor/medical information sensed from a user may be received/transmitted from/to the server, via a base station over the air interface 216. In one embodiment, the transmit/receive element 222 may be an antenna configured to transmit and/or receive RF signals. In an embodiment, the transmit/receive element 222 may be an emitter/detector configured to transmit and/or receive IR, UV, or visible light signals, for example. In yet another embodiment, the transmit/receive element 222 may be configured to transmit and/or receive both RF and light signals. It will be appreciated that the transmit/receive element 222 may be configured to transmit and/or receive any combination of wireless signals. The transceiver 220 may be configured to modulate the signals that are to be transmitted by the transmit/receive element 222 and to demodulate the signals that are received by the transmit/receive element 222.

The processor 218 of the device 200 may be coupled to, and may receive user input data from, the speaker/microphone 224, the keypad 226, the display/touchpad 228 (e.g., a liquid crystal display (LCD) display unit or organic light-emitting diode (OLED) display unit) and/or the peripherals 238 (e.g., sensors or digital camera). The processor 218 may also output user data or digital instructions to the speaker/microphone 224, the keypad 226, the display/touchpad 228 and/or the peripherals 238. In addition, the processor 218 may access information from, and store data in, any type of suitable memory, such as the non-removable memory 230 and/or the removable memory 232. The non-removable memory 230 may include random-access memory (RAM), read-only memory (ROM), a hard disk, or any other type of memory storage device. The removable memory 232 may include a subscriber identity module (SIM) card, a memory stick, a secure digital (SD) memory card, and the like. In other embodiments, the processor 218 may access information from, and store data in, memory that is not physically located on the device 200, such as on a server or a home computer (not shown).

The processor 218 may receive power from the power source 234, and may be configured to distribute and/or control the power to the other components in the device 200. The power source 234 may be any suitable device for powering the device 200. For example, the power source 234 may include one or more dry cell batteries (e.g., nickel-cadmium (NiCd), nickel-zinc (NiZn), nickel metal hydride (NiMH), lithium-ion (Li-ion), etc.), solar cells, fuel cells, and the like.

The processor 218 may also be coupled to the GPS chipset 236, which may be configured to provide location information (e.g., longitude and latitude) regarding the current location of the device 200. In addition to, or in lieu of, the information from the GPS chipset 236, the device 200 may receive location information over the air interface 216 from a base station and/or determine its location based on the timing of the signals being received from two or more nearby base stations. It will be appreciated that the device 200 may acquire location information by way of any suitable location-determination method while remaining consistent with an embodiment.

The processor 218 may further be coupled to other peripherals 238, which may include one or more software and/or hardware modules that provide additional features, functionality and/or wired or wireless connectivity. For example, the peripherals 238 may include an accelerometer, an e-compass, a satellite transceiver, a digital camera (for photographs and/or video), a universal serial bus (USB) port, a vibration device, a television transceiver, a hands free headset, a Bluetooth® module, a frequency modulated (FM) radio unit, a digital music player, a media player, a video game player module, an Internet browser, a Virtual Reality and/or Augmented Reality (VR/AR) device, an activity tracker, and the like. The peripherals 238 may include one or more sensors. The sensors may be one or more of a gyroscope, an accelerometer, a hall effect sensor, a magnetometer, an orientation sensor, a proximity sensor, a temperature sensor, a time sensor; a geolocation sensor, an altimeter, a light sensor, a touch sensor, a magnetometer, a barometer, a gesture sensor, a biometric sensor, a humidity sensor and the like.

The processor 218 may perform a digital instruction generation, a sensing data collection, an execution input, an outcome analysis, communication with a database and a security function.

Based on the mechanism of action in and the therapeutic hypothesis and digital therapeutic hypothesis for amnestic MCI and AD, a doctor (e.g., a second user) may prescribe DTx, which are realized in a digital apparatus and/or an application for treating MCI and AD for the corresponding patient. In one example, the processor 218 may be configured to provide a prescription of the DTx to a patient as a specific behavioral instruction that the patient may execute based on the interaction between the neuro-humoral factors for MCI and AD and the patient's behaviors/environments. For example, the neuro-humoral factors may include, but are not limited to, sex steroid hormone, IGF-2, wnt/β-catenin, BAG1, CREB, inflammation factors, corticosteroids, neurohormones, and all types of neuro-humoral factors that may cause myopia can be considered.

The processor 218 may generate digital instructions based on the inputs from the doctor. In this case, the processor 218 may generate digital instructions based on information collected from/by the doctor when diagnosing a patient. Also, the processor 218 may generate digital instructions based on the information received from the patient. For example, the information received from the patient may include the patient's basal factors, medical information, and DTx literacy. In this case, the basal factors may include the patient's activity, heart rates, sleep, meals (e.g., nutrition and calories), and the like. The medical information may include the patient's electronic medical record (EMR), family history, genetic vulnerability, genetic susceptibility, and the like. The DTx literacy may include the patient's accessibility to the digital therapy instructions and the apparatus, an acceptance posture, and the like.

Figure 5A:
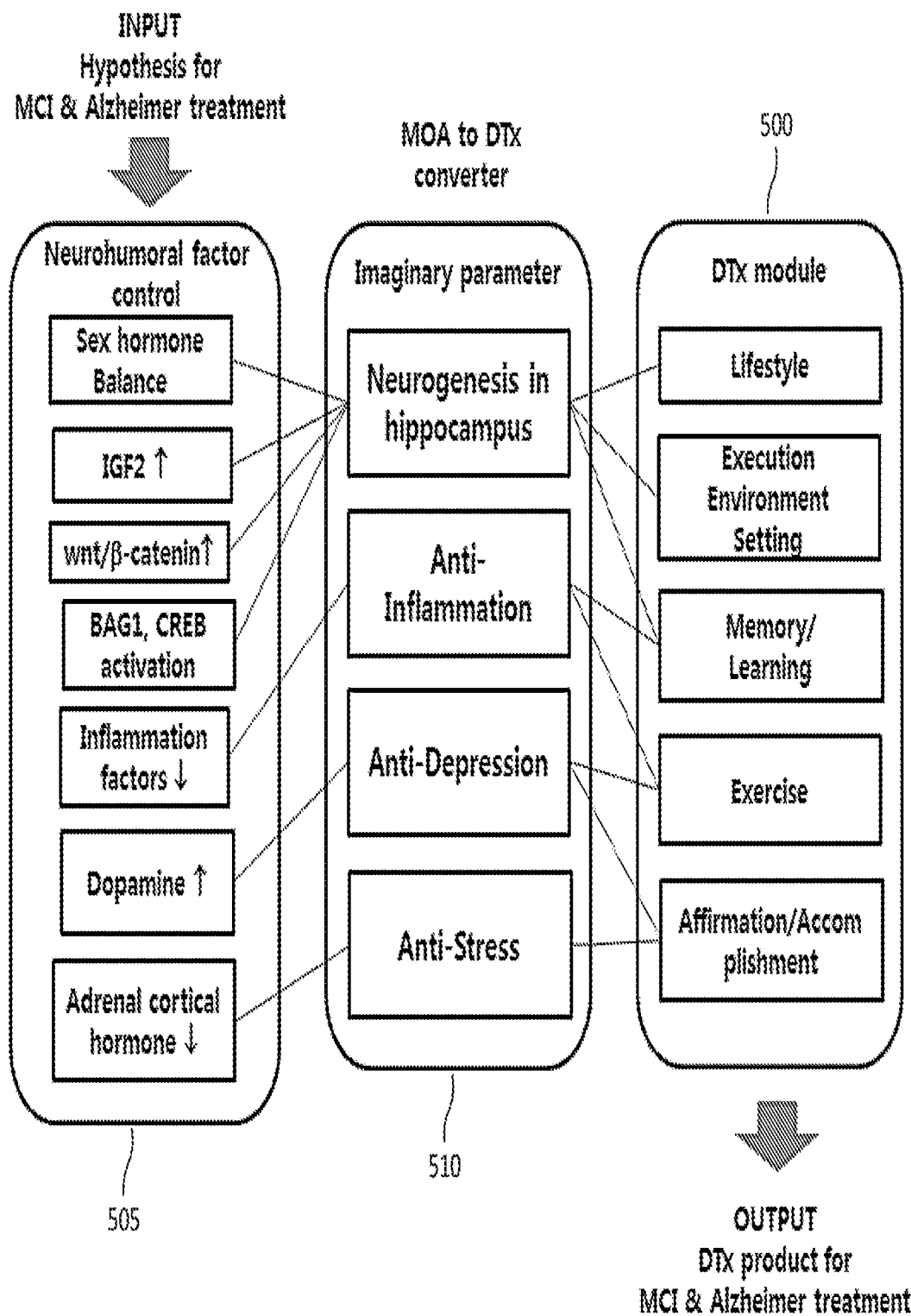
FIG. 5A is a diagram illustrating example modules to implement digital therapeutics for treating or inhibiting progression of MCI and AD.

The processor 218 may reflect the MOA and the therapeutic hypothesis for MCI and AD in order to utilize one or more imaginary parameters and generate a digital module. In this case, the imaginary parameters may be deduced in term of neurogenesis in hippocampus, anti-inflammation, anti-stress and anti-depression, considering the patient's environments, behaviors, emotions, and cognition. The imaginary parameters will further be described in detail as shown in FIG. 5A.

The processor 218 may generate digital instructions particularly designed to allow a patient to have therapeutic effect, and provide the instructions to the patient. For example, the processor 218 may generate specific digital instructions in each DTx module.

The processor 218 may perform sensing data collection and execution input that can collect the patient's execution outcomes of the digital instructions. Specifically, the processor 218 is configured to sense the patient's adherence to the digital instructions and allow a patient to directly input the execution outcomes of the digital instructions, and thus serve to output the patient's execution outcomes of the digital instructions.

The processor 218 may collect the patient's behavior adherence or participation in predetermined periods, and report the patient's behavior adherence or participation to external systems. Therefore, a doctor may continue to monitor an execution course of the digital instructions through the application even when a patient does not directly visit a hospital.

The database can store the MOA and the therapeutic hypothesis of MCI and AD, the digital instructions provided to the user and the user's execution outcome data. Although it is not shown in FIG. 2, the database 050 may be included in the device 200 for treating MCI and AD. Alternatively or additionally, the database 050 may be provided in an external server.

Meanwhile, a series of loops including inputting the digital instructions, outputting the patient's execution outcomes of the digital instructions and evaluating the execution outcomes can be repeatedly executed several times. In this case, the processor may generate patient-customized digital instructions for this cycle by reflecting the patient's digital instructions provided in the previous cycle, the output values and the evaluation.

As described above, the device 200 for inhibiting progression of and treating amnestic MCI and AD can inhibit the progression of amnestic MCI and AD and provide improved therapeutic effect by deducing a MOA, therapeutic hypothesis and digital therapeutic hypothesis based on the neuro-humoral factors of amnestic MCI and AD. The device 200 may provide digital instructions based on these findings, and collect and analyze the execution outcomes.

Figure 3:
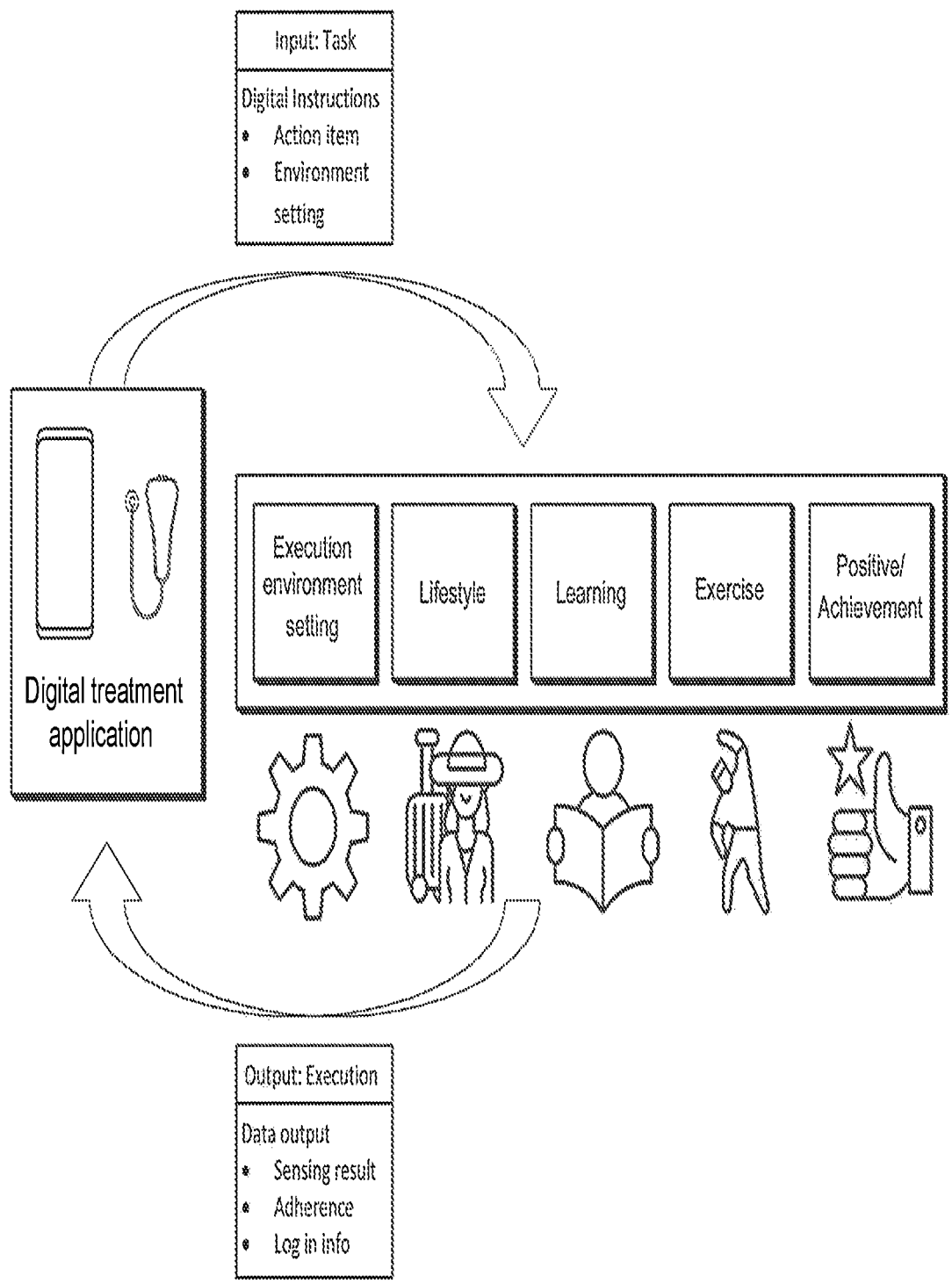
FIG. 3 is a diagram illustrating an example input and output loop of a user device for treating or inhibiting progression of MCI and AD.

FIG. 3 is a diagram illustrating an example input and output loop of a user device for treating or inhibiting progression of MCI and AD, which may be used in combination with any of other embodiments described herein.

Referring to FIG. 3, the digital application for treating MCI and AD according to one embodiment may provide a corresponding digital prescription for a patient in the form of instructions. The execution outcomes of the corresponding digital instructions may be recursively entered into the application as an input.

The digital instructions provided to the patient may include specific action instructions and control of the patient's light environments. As shown in FIG. 3, the digital instructions may include, but are not limited to, execution environment setting, lifestyle, learning, exercise and positive/achievement.

The patient's execution outcomes of the digital instructions may comprise: (1) log-in/log-out information for instructions and execution; (2) adherence information sensed as passive data such as exercise, heart rates associated with the stress, a change in oxygen saturation, and the like; and (3) directly input information on the patient's execution outcomes.

Figure 4:
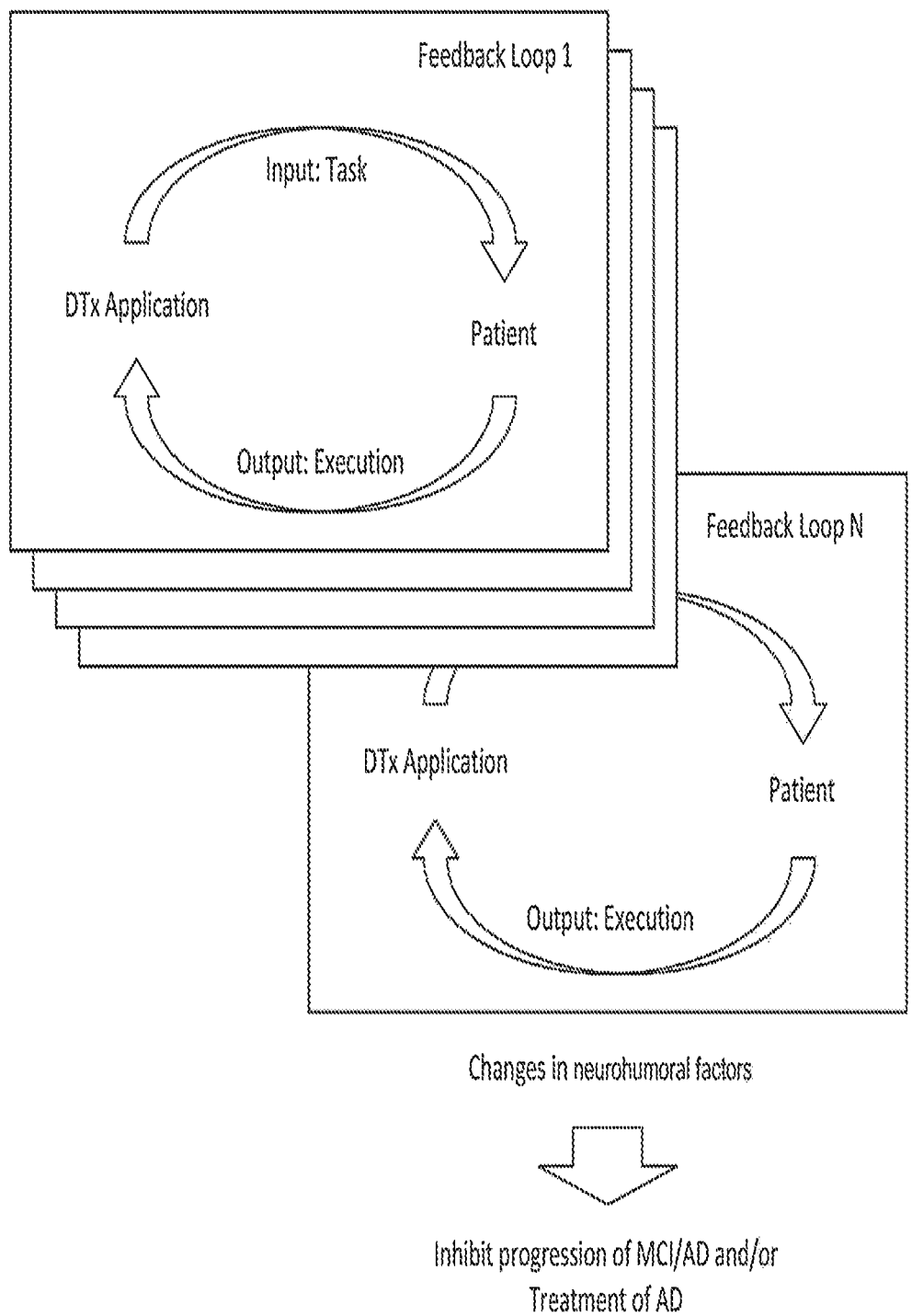
FIG. 4 is a diagram illustrating an example feedback loop for treating or inhibiting progression of and treating MCI and AD.

FIG. 4 is a diagram illustrating an example feedback loop for treating or inhibiting progression of and treating MCI and AD, which may be used in combination with any of other embodiments described herein.

Referring to FIG. 4, inhibition of the progression of and treatment of MCI and AD may be achieved by repeatedly executing the aforementioned single feedback loop of FIG. 3 multiple times to regulate the neuro-humoral factors.

In the case of MCI and AD, constant digital therapy and observation is needed. Due to these characteristics, inhibitory and therapeutic effects on progression of the MCI and AD may also be achieved by gradual improvement of an instruction-execution cycle in the feedback loop, compared to the simply repeated instruction-execution cycle without the feedback loop during the corresponding course of therapy. For example, the digital instructions and the execution outcomes for the first cycle are given as input values and output values in a single loop, but new digital instructions can be generated by reflecting input values and output values generated in this loop using a feedback process of the loop to adjust the input for the next loop when the feedback loop is executed N times. This feedback loop may be repeated to deduce patient-customized digital instructions and maximize a therapeutic effect at the same time.

As such, in the digital apparatus and the application, the patient's digital instructions provided in the previous cycle (e.g., $(N-1)^{th}$ cycle), and the data on instruction execution outcomes may be used to calculate the patient's digital instructions and execution outcomes in the current cycle (e.g., $N^{th}$ cycle). That is, the digital instructions in the next loop can be generated based on the patient's digital instructions and execution outcomes of the digital instructions calculated in the previous loop. In this case, various algorithms and statistical models may be used for the feedback process, when necessary.

As described above, in the digital apparatus and the application for treating MCI and AD, it is possible to optimize the patient-customized digital instructions suitable for the patient through the rapid feedback loop.

Figure 5B:
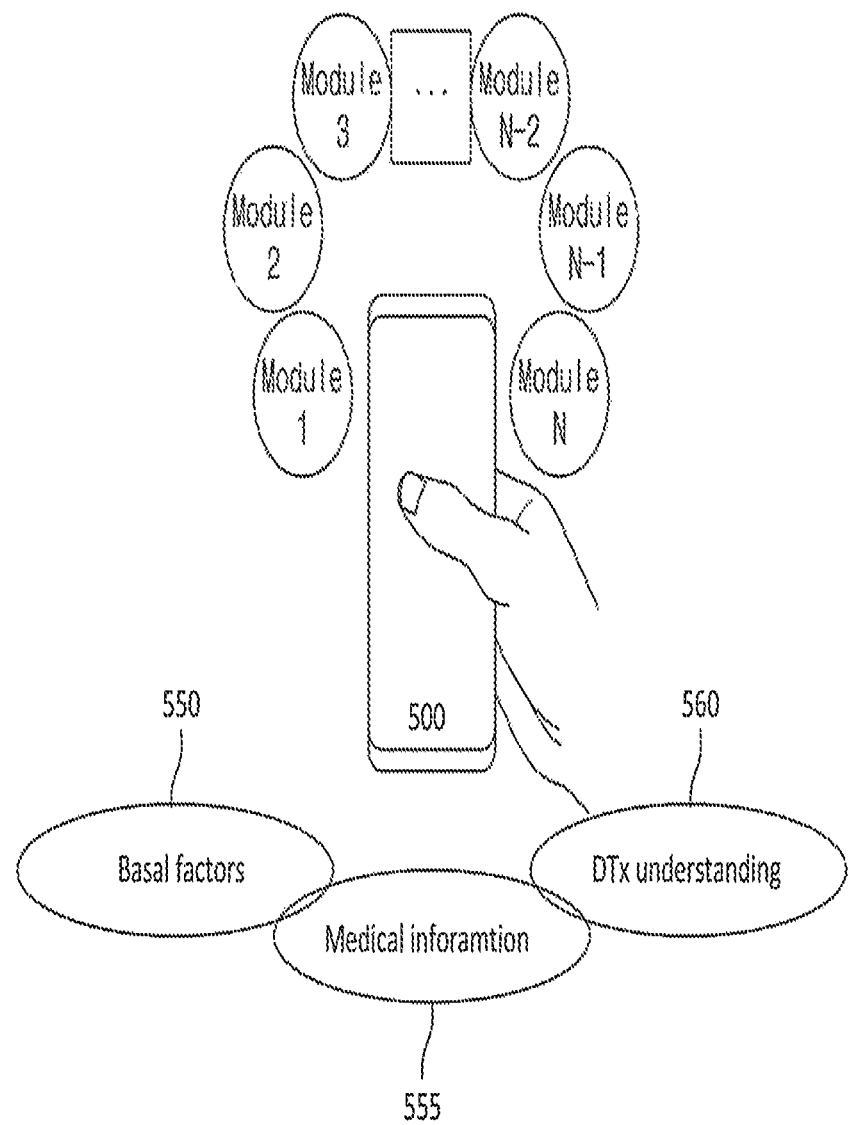
FIG. 5B is a diagram illustrating example background factors that support a user device for treating or inhibiting progression of MCI and AD.

FIG. 5A is a diagram illustrating example modules to implement digital therapeutics for treating or inhibiting progression of MCI and AD, which may be used in combination with any of other embodiments described herein. FIG. 5B is a diagram illustrating example background factors that support a user device for treating or inhibiting progression of MCI and AD, which may be used in combination with any of other embodiments described herein.

As shown in FIG. 5A, when the therapeutic hypothesis based on the MOA of MCI and AD is created, targeted neuro-humoral factors 505 (e.g., sex steroid hormone, IGF-2, wnt/β-catenin, BAG1, CREB, inflammation factors, corticosteroids and neurohormones, etc.) can be deduced. Imaginary parameters 510 may be utilized to allow specific instructions to correspond to the regulation of these neuro-humoral factors 505. Modules 500 to treat MCI and AD may be deduced using the "neuro-humoral factor-imaginary parameter-module" interrelation. Each of the modules 500 may be described in the form of modular instructions in further detail with reference to FIGS. 7A-E. In this case, each of the modules 500 is a basic design unit for digital therapeutics realized in the actual digital apparatus or the application, and is a collection of specific instructions.

Specifically, referring to FIG. 5A, the neuro-humoral factors 505 deduced based on the MOA and the therapeutic hypothesis for MCI and AD may include, but are not limited to, sex steroid hormone, IGF-2, wnt/β-catenin, BAG1, CREB, inflammation factors, corticosteroids and neurohormones. To treat MCI and AD, imbalance of the neurohumoral factors may be tackled by balancing sex steroid hormone, increasing secretion of IGF-2, balancing wnt/β-catenin, increasing secretion of BAG1 and CREB, decreasing secretion of inflammation factors and corticosteroids and increasing secretion of neurohormones.

To further elaborate on the "neuro-humoral factor-imaginary parameter-DTx module" interrelation from a molecular biological, neurophysiological and pathological perspective, each of the neuro-humoral factors may be illustrated in specified categories as i) neurogenesis in hippocampus related to declarative memory-semantic memory consolidation, ii) anti-inflammation related to episodic memory consolidation, iii) anti-stress and ant-depression.

Although almost all mammals, including human, undergo life-long continuous neurogenesis, generally active adult neurogenesis occurs only in limited brain areas where neurogenesis is especially apparent (the subgranular zone (SGZ) in the dentate gyrus of the hippocampus and the subventicular zone (SVZ) of the laternal venticles). Adult neurogenesis of the central nervous system (CNS) in the other areas is known to be highly limited under general physiological conditions.

What is first observed about the progression of amnestic MCI and AD is the damage in declarative memory-semantic memory. In order to treat or inhibit this progression, neurogenesis in hippocampus has been recently receiving attention, and genes and proteins related to neurogenesis may be used as the targets of dementia treatment drug developments.

Neurogenesis in hippocampus is related to sex steroid hormone, IGF-2, wnt/β-catenin, BAG1, CREB, or the like.

Decline in female hormone after menopause (i.e. imbalance in sex steroid hormone) illustrates relatively high dementia prevalence rate of women, which is as twice as higher than that of men. In the randomized controlled trial (RCT) on the impact of hormone replacement therapy (HRT) on cognitive function targeting postmenopausal women, only the HRT treatment group had demonstrated a significant increase in Montreal Cognitive Assessment (MoCA) score before and after the treatment, in other words, an increase in cognitive ability. MoCA is a type of screening test to detect MCI and AD and has been adopted in numerous hospitals.

Light is known to help enhance human cognitive function. However, the neurobiological mechanism of light in this positive sense has yet been acknowledged. Recently, research using a trained mouse on the timing of daily rhythms reported the relevance between long days and the increase of IGF-2(locally secreted IGF), and between long days and the enhancement of long-term recognition memory in hippocampus.

Wnt signaling plays a significant role in nervous system development and adult synaptic plasticity. Particularly on learning and memory, Wnt signaling may take on a key role in normal functioning of hippocampus. Wnt/β-catenin E2/E4 balance relates to memory consolidation-storage-recollection through learning in the declarative memory area.

BAG gene relates to neurodegenerative diseases associated with ageing such as AD and is a crucial factor of neuronal differentiation. It may take a direct role in memory-related synaptic plasticity of CREB (cAMP Response Element Binding protein). BAG1/CREB relates to neurogenesis in hippocampus, and it has been recently reported that neurogenesis in hippocampus is controlled by the defense response resulted from treat- and extinction-signaling brain network.

By corresponding the aforementioned neuro-humoral factors 505 to the action instructions of the DTx module 500 using the imaginary parameter 510 of neurogenesis in hippocampus, dementia therapeutic effect can be derived from controlling/ameliorating the imbalance or deficiency of the neuro-humoral factor(s) through action instructions. The examples of specifically connecting the action instructions related to neurogenesis in hippocampus with the neuro-humoral factors can include amelioration of sex steroid hormone through dietary control, increase in IGF-2 secretion through good light environment, recovery of wnt/β-catenin balance through learning activities, and activation of BAG1/CREB brain neural network through experiences with treat- and extinction-situations.

Anti-inflammation is associated with inflammation factors. Inflammation factors may disturb consolidation of episodic memory and aggravate dementia by interrupting recollection of the declarative memory area. By corresponding inflammation factors to the action instructions of the DTx module using the imaginary parameter of anti-inflammation, dementia therapeutic effect can be derived from controlling/ameliorating the high inflammation level.

Anti-stress relates to corticosteroid hormone including cortisol and glucocorticoid. Anti-depression relates to neural hormone including dopamine, noradrenaline and somatostatin. The imbalance in corticosteroid steroid hormone and neural hormone negatively affect neurogenesis and leaning in hippocampus. By corresponding corticosteroid steroid hormone and neural hormone to the action instructions of the DTx module using the imaginary parameter of anti-stress and anti-depression, dementia therapeutic effect can be derived from controlling/ameliorating the imbalance in corticosteroid steroid hormone and neural hormone. The action instructions related to anti-inflammation, anti-stress and anti-depression can include safe and familiar execution environment, nutritious diet along with exercising and normal sleep inducing.

To summarize, the control of each neuro-humoral factor 505 may correspond to the DTx modules 500 by using imaginary parameters 510 such as neurogenesis in hippocampus, anti-inflammation, anti-stress and anti-depression. Also, the specific digital instructions for each module may be made based on the DTx modules. At the same time, the digital instructions can include execution environment setting and modules, such as lifestyle, learning, exercise, affirmation-achievement or similar module. However, the modules of this embodiment is not limited thereto.

The control of each of the neurohumoral factors 505 corresponded to the DTx module 500 using imaginary parameters 510 such as neurogenesis in hippocampus, anti-inflammation, anti-stress and anti-depression. And then, specific digital instructions may be generated for each module based on the converted modules. In this case, the digital instructions may include execution environment set-ups and modules (e.g., lifestyle, learning, exercise, affirmation-achievement), which can be output by monitoring. However, these modules 500 are given by way of illustration only, and are not intended to be limiting to the modules 500.

Referring to FIG. 5B, the background factors may be considered together in the design of the modules in the digital apparatus and the application for treating MCI and AD according to one embodiment of the present invention.

In this case, the background factors are elements necessary for correction of clinical trial outcomes during verification of the clinical effectiveness of digital therapy for MCI and AD. Specifically, in the background factors shown in FIG. 5B, the basal factors 550 may include, but are not limited to, activity, heart rates, sleep, meals (nutrition and calories), and the like. The medical information 555 may include, but are not limited to, EMR, family history, genetic vulnerability, and susceptibility, and the like. The medical information may have been written when a patient visited a hospital. The DTx literacy or understanding 560 may include, but is not limited to, the patient's accessibility to the digital therapy instructions and the apparatus, and an acceptance posture.

Figures 6A, 6B:
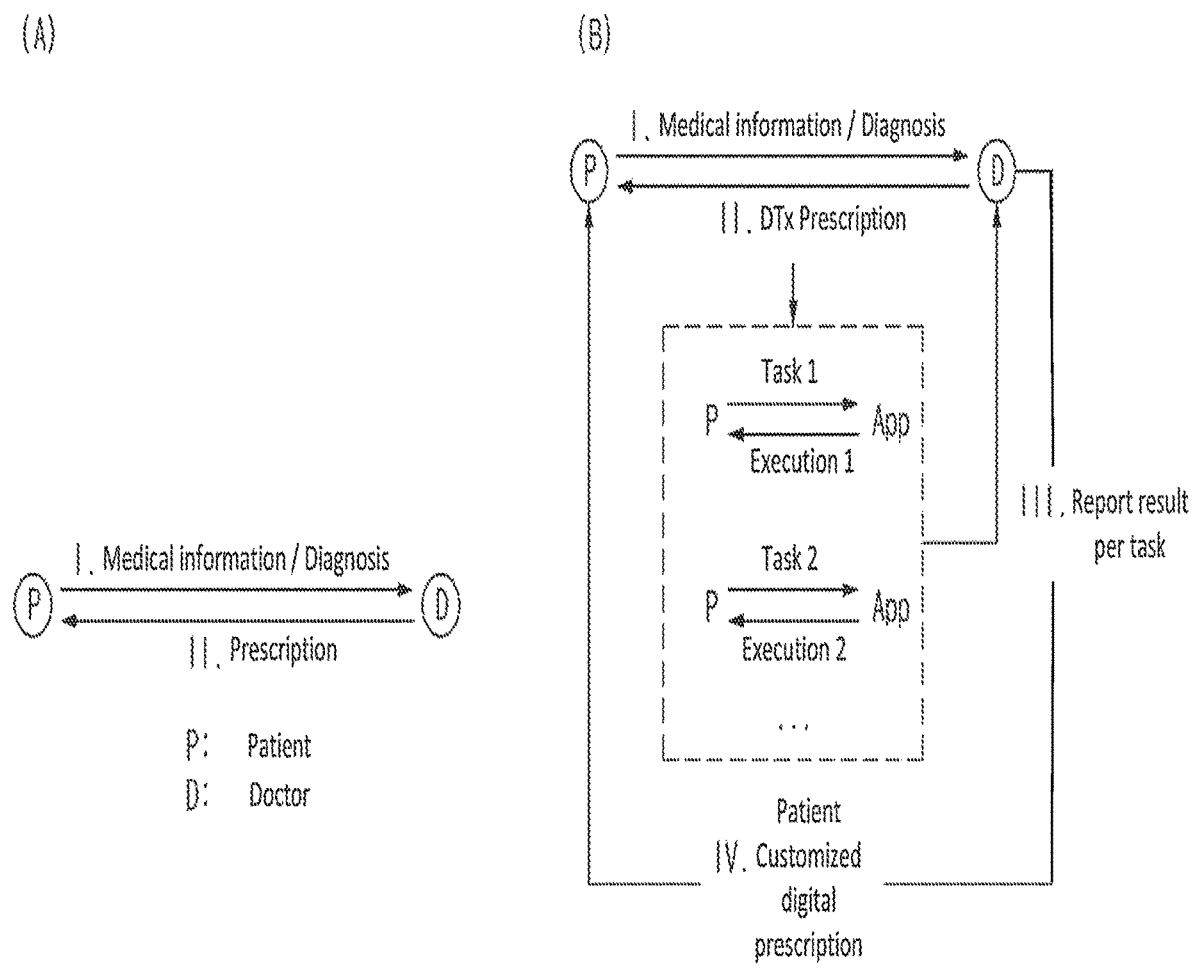
FIG. 6A is a diagram illustrating an example method of assigning a patient-customized prescription.
FIG. 6B is a diagram illustrating an example method of assigning a patient-customized digital prescription.

FIG. 6A is a diagram illustrating an example method of assigning a patient-customized prescription, which may be used in combination with any of other embodiments described herein. FIG. 6B is a diagram illustrating an example method of assigning a patient-customized digital prescription based on the analysis of a plurality of digital instructions and execution outcomes of the digital instructions, which may be used in combination with any of other embodiments described herein.

In this way, when the digital apparatus and the application for treating MCI and AD are used, a medical professional (e.g., doctor) may check the patient's instructions and execution outcomes for a given period and adjust the types of modules for treating MCI and AD, and the instructions for each module in a patient-customized manner, as shown in FIG. 6B.

FIG. 7A is a diagram illustrating an example digital instruction for an execution environment setting, which may be used in combination with any of other embodiments described herein. FIG. 7B is a diagram illustrating an example digital instruction for a lifestyle module, which may be used in combination with any of other embodiments described herein. FIG. 7C is a diagram illustrating an example digital instruction for a memory/learning module, which may be used in combination with any of other embodiments described herein. FIG. 7D is a diagram illustrating an example digital instruction for an exercise module, which may be used in combination with any of other embodiments described herein. FIG. 7E is a diagram illustrating an example digital instruction for a positive/achievement module, which may be used in combination with any of other embodiments described herein.

For digital therapy of MCI and AD, it is important for the participants to feel interest in the digital therapy and voluntarily take part in the therapy as continuous treatment. In this context, the modules may be configured by adding game elements to each module. In the digital apparatus and the application for inhibiting progression of and treating amnestic MCI and AD, as will be described below, each module comprises a collection of specific instructions.

Referring to FIG. 7A, specific examples of instructions for execution environment setups and a method of collecting output data are shown. In this case, the execution environment setups can be included as part of the configuration of the digital instruction generation as described above. The other modules shown in FIG. 7B to 7E may be executed under a bright, familiar and relaxing environment at execution environment setup of FIG. 7A.

Brightness setup may include, but is not limited to, setting the brightness of the digital instruction execution environment using an illuminance sensor or an IoT lamp, creating a living environment where a person can be exposed to bright surroundings, for example, for at least 16 hours a day.

Coziness or familiarity setup can include application environment setting (e.g., contents that might help the patient recall past memories such as the patient's favorite songs, scenes and lines from the patient's favorite movies, family pictures, documentary photography, etc.) and location setting configured to help patients recall memories in familiar and friendly surroundings for them during the execution of the instructions.

Comport or relaxation setup can include application environment setting (e.g., contents that might help relieve stress such as background wallpaper, music, tone, etc.) which provides a relaxing atmosphere to execute the instructions, and location setting which provides restfulness during the execution of the instructions.

FIGS. 7B-E show examples of specific instructions for each module, and methods of collecting output data. In these embodiments, modules can include lifestyle, learning, exercise and affirmation (or positive)-achievement modules.

Referring to FIG. 7B, specific examples of instruction for a lifestyle module, and a method of collecting output data are shown. In this case, the lifestyle module can be included as part of the configuration of the digital instruction generation as described above.

The new experience and travel instructions can include a trip to a new place to experience new environments once in every week or two week. The new experience and travel (instructions) can include recording (execution) using journals or various digital media.

Balance of sex hormones instruction aims at recovering from radical imbalance in sex steroid hormones due to ageing or climacterium. Particularly, climacteric women who have undergone radical changes in sex hormones are recommended to avoid HRT(hormone replacement therapy) or severe diet entailing radical loss of fat. Regaining the balance of sex hormones instruction through meals reflecting nutritional balance may include, but is not limited to, meal recording and nutrition evaluation(execution).

Referring to FIG. 7C, specific examples of instructions for a learning module and a method of collecting output data are shown. In this case, the learning module may be included as part of the configuration of the digital instruction generation as described above.

Specifically, the instructions of the learning module can include behavioral instructions that make patients constantly repeat and recall familiar things in a relaxed atmosphere. In case of the learning module, the first user's execution can be executed in the form of game record of log book which promotes memory and learning. Also, the comfortable environment for associative learning can be provided with the background, tone and music settings of the DTx. For example, the instructions of the learning module can induce the user to listen to relieving music or to smell good scents.

Referring to FIG. 7D, specific examples of instructions for an exercise module and a method of collecting output data are shown. In this case, the physical exercise module may be included as part of the configuration of the digital instruction generation as described above.

The exercise module may include a series of behavioral instructions which entail, for example, 20 minutes of acute exercise on a regular basis (e.g., three times a week).

Specifically, the behavioral instructions of the exercise module may include the method to collect the execution outcomes with the sensing data collection using neuronal biofeedback devices (e.g., EEG, ECG, EMG, EDG, etc.) or general sensors (e.g., activity, HR, etc.), or the method for the patient to directly input the execution outcomes using the execution input as described above. In this case, the exercise instructions can be organized according to the age and the physical condition of the patient, using the exercise therapy widely used by doctors or motor therapists.

In case of the exercise module, the first user can execute the behavioral instructions by writing an exercise journal, checking heart rates, or getting a personal training (PT) coach.

Referring to FIG. 7E, specific examples of instructions for an affirmation (or positive)/achievement module and a method of collecting output data are shown. In this case, the physical exercise module may be included as part of the configuration of the digital instruction generation as described above.

Specifically, the affirmation(or positive)/achievement module can include instructions that stimulate the secretion of dopamine through the patient's execution of tasks and the fulfillment of the completion. In this case, task completion instruction may be an instruction that makes patient feel a sense of accomplishment by completing the given tasks, wherein patients can update the tasks in accordance with the deadline and their voluntary participation can be induced. For example, the specific format of game can vary from learning, spot the difference or find the difference game, quiz, etc.

Particularly, that part realized as a format of quiz from the affirmation (or positive)/achievement module is further expected to enhance patient's health information literacy and DTx literacy. The enhancement in such abilities may be needed for a patient to constantly take part in the therapy and improve the patient's performance status.

In case of the affirmation (or positive)/achievement module, the first user can execute the task in ways such as self-feedback, self-reward, reward from a doctor based on the doctor-patient relationship and so on.

As mentioned above, long-term constant participation from the patients may be needed for the digital therapy. Diligent participation during the therapy can generate a compliment(reward) task in the affirmation (positive)/ achievement module so that the patient can feel a sense of accomplishment. In the compliment task, patients who actively participate in the therapy can be compensated with reward and trust in patient-guardian and/or patient-doctor relationship.

Meanwhile, progression of MCI and AD and aging is closely related. Particularly, in the old aging period, there is a wide gap in standards set for new lifestyles, learning, exercise, and affirmation (or positive)/achievement, depending on age, sex, personality and preference. To bridge the gap, it is desirable to propose customized digital instructions for each module concerning the individual characteristics of each patient. Particularly, the instructions that require intercommunication with the application can be developed by combining with big data analysis and artificial intelligence analysis.

The digital instructions illustrated in FIG. 7B to FIG. 7E are given by way of illustration only, and are not intended to limit the present invention. For example, the digital instructions provided to the patient may be set in various manners, when necessary.

Figure 8:
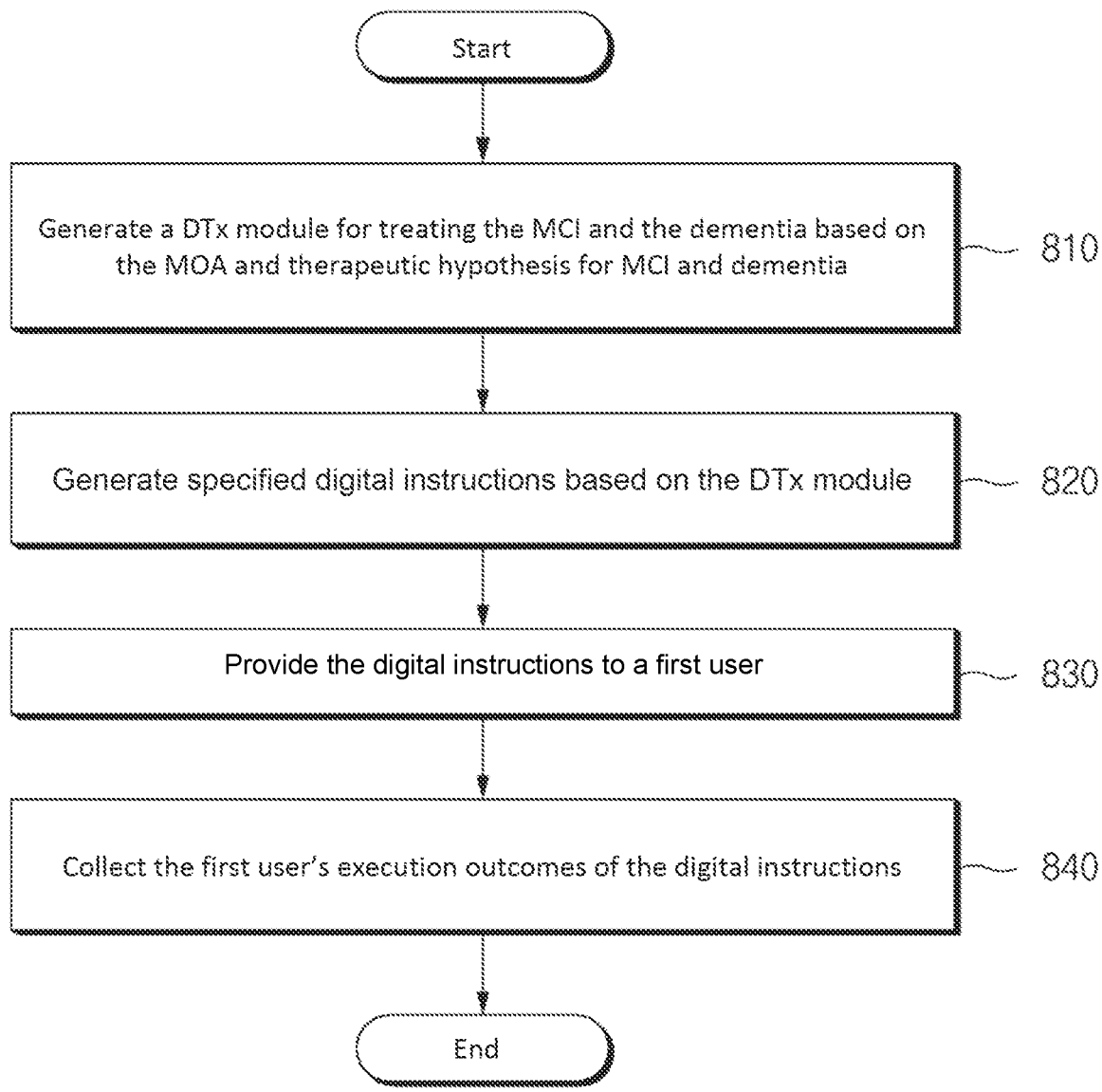
FIG. 8 is a diagram illustrating an example procedure using an digital application for treating or inhibiting progression of MCI and AD.

FIG. 8 is a diagram illustrating an example procedure using a digital application for treating or inhibiting progression of MCI and AD, which may be used in combination with any of other embodiments described herein.

Referring to FIG. 8, at step 810, the digital application for treating MCI and AD according to one embodiment can first generate a DTx module for treating MCI and AD based on the MOA and the therapeutic hypothesis of MCI and AD. In this case, the DTx module may be generated based on the neuro-humoral factors (e.g., sex steroid hormone, IGF-2, wnt/(β-catenin, BAG1, CREB, inflammation factors, corticosteroids, neurohormones, etc.) for MCI and AD.

Alternatively or additionally, at step 810, the digital therapeutics module may be generated based on the inputs from a medical professional (e.g., doctor). In this case, a DTx module may be generated based on the information collected by the medical professional when diagnosing a patient, and the prescription outcomes recorded based on the information. Also, at step 810, the DTx module may be generated based on the information (e.g., basal factors, medical information, digital therapeutics literacy, etc.) received from the patient.

At step 820, specified digital instructions may be generated based on the DTx module. For example, a DTx module may be generated by applying imaginary parameters about the patient's environments and behavioral aspects (e.g., neurogenesis in hippocampus, anti-inflammation, anti-stress and anti-depression) to the MOA and the therapeutic hypothesis for MCI and AD. This DTx module is described with reference to FIGS. 5A and 5B, and thus description thereof will be omitted.

In this case, the digital instructions may be generated for at least one of execution environment setting, lifestyle, learning, exercise and affirmation (or positive)/achievement. Description of the execution environment setups and the specific digital instructions for each of the modules is as described in FIGS. 7A-E.

At step 830, the digital instructions may be provided to the patient. In this case, the digital instructions may be provided in the form of digital instructions which are associated with behaviors, emotions and cognition, and in which the patient's instruction adherence such as lifestyle and physical exercise may be monitored using a sensor, or provided in the form of digital instructions in which a patient is allowed to directly input the execution outcomes.

After the patient executes the presented digital instructions, at step 840, the patient's execution outcomes of the digital instructions may be collected. For example, the execution outcomes of the digital instructions may be collected by monitoring the patient's adherence to the digital instructions as described above, or allowing the patient to input the execution outcomes of the digital instructions.

Meanwhile, the digital application for treating MCI and AD according to one embodiment can repeatedly execute operations several times, wherein the operations include generating the digital instruction and collecting the patient's execution outcomes of the digital instructions. In this case, the generating of the digital instruction may include generating the patient's digital instructions for this cycle based on the patient's digital instructions provided in the previous cycle and the execution outcome data on the patient's collected digital instructions.

As described above, the MOA, the therapeutic hypothesis and the digital therapeutic hypothesis may be deduced considering neuro-humoral factors of the progression of amnestic MCI and AD. Patients will be given digital tasks based on these findings, and their execution and completion of tasks will be collected and analyzed in order to effectively inhibit the progression of amnestic MCI and AD and offer improved therapeutic effect.

Although the digital apparatus and the application for treating MCI and AD have been described in terms of MCI and AD therapy, the present invention is not limited thereto. For the other diseases other than MCI and AD, the digital therapy may be executed substantially in the same manner as described above.

Figure 9:
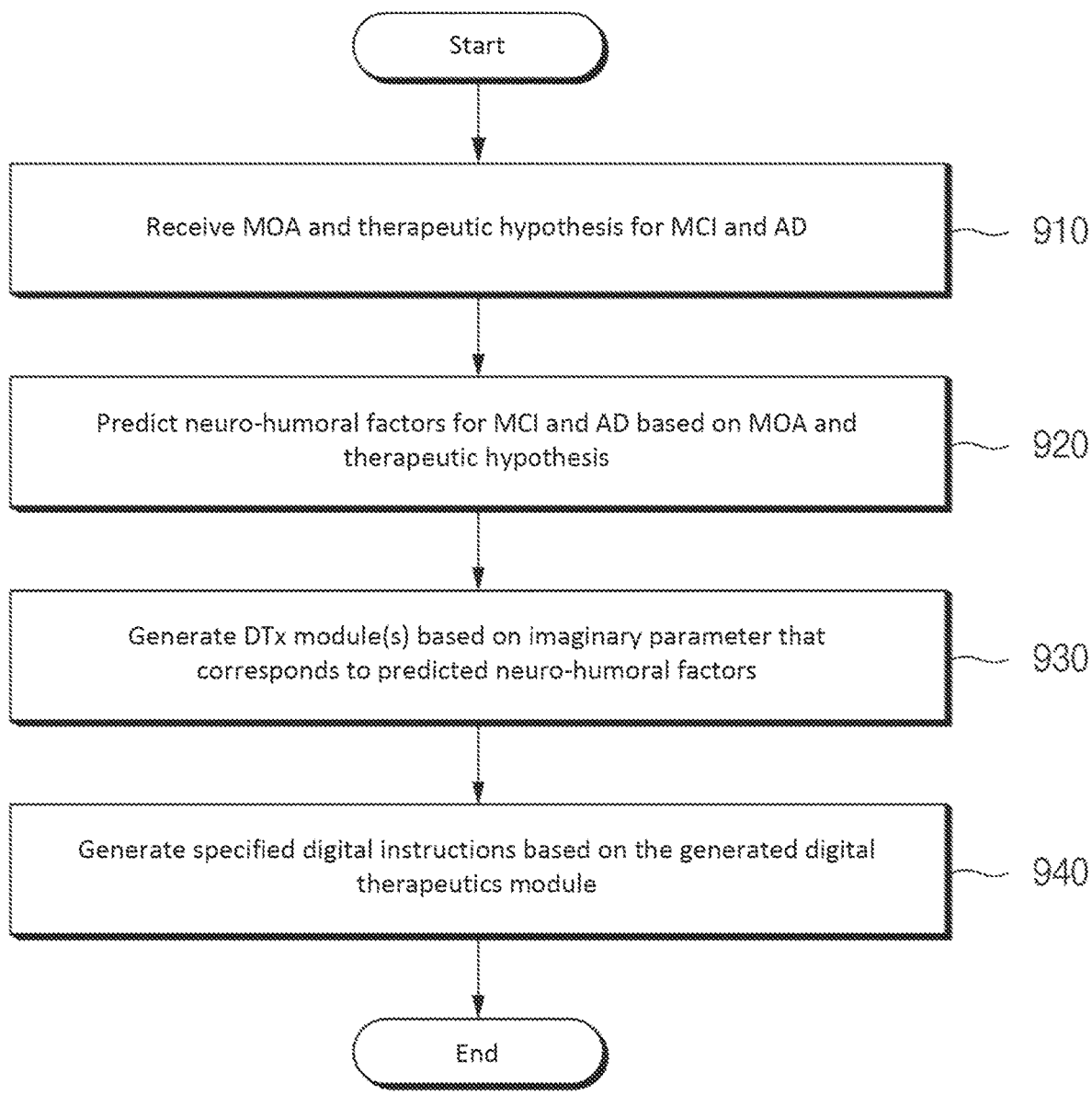
FIG. 9 is a diagram illustrating an example procedure for generating digital instructions to treat or inhibit progression of MCI and AD.

FIG. 9 is a diagram illustrating an example procedure for generating digital instructions to treat or inhibit progression of MCI and AD, which may be used in combination with any of other embodiments described herein.

FIG. 9 further describes the process of generating the module and the specified digital instructions for treating MCI and AD based on the MOA and the therapeutic hypothesis of MCI and AD as described in FIGS. 5A, 5B and 8.

At step 910, the MOA and the therapeutic hypothesis for MCI and AD can be input. In this case, the MOA and the therapeutic hypothesis for MCI and AD may be previously deduced through the literature search and expert reviews on the systematic related clinical trials on MCI and AD, as described above.

At step 920, neuro-humoral factors for MCI and AD may be predicted from the input MOA and therapeutic hypothesis. In this case, the neuro-humoral factors for MCI and AD predicted at step 920 may be deduced in the form of sex steroid hormone, IGF-2, wnt/β-catenin, BAG1, CREB, inflammation factors, corticosteroids, neurohormones, or the like. These neuro-humoral factors have been described in detail with reference to FIG. 5A, and thus description thereof will be omitted.

At step 930, a DTx module may be generated based on the predicted neuro-humoral factors corresponding to imaginary parameters. Here, the imaginary parameters may serve as converters that convert the neuro-humoral factors for MCI and AD into a DTx module, and this procedure is to set the physiological interrelation between the neuro-humoral factors and the environmental and behavioral factors, as shown in FIG. 5A.

At step 940, specified digital instructions may be generated based on the generated digital therapeutics module. In this case, the specific digital instructions may be generated by the execution environment setup, lifestyle, learning, exercise and affirmation (or positive)/achievement modules, which were described with reference to FIGS. 7A-E.

Figure 10:
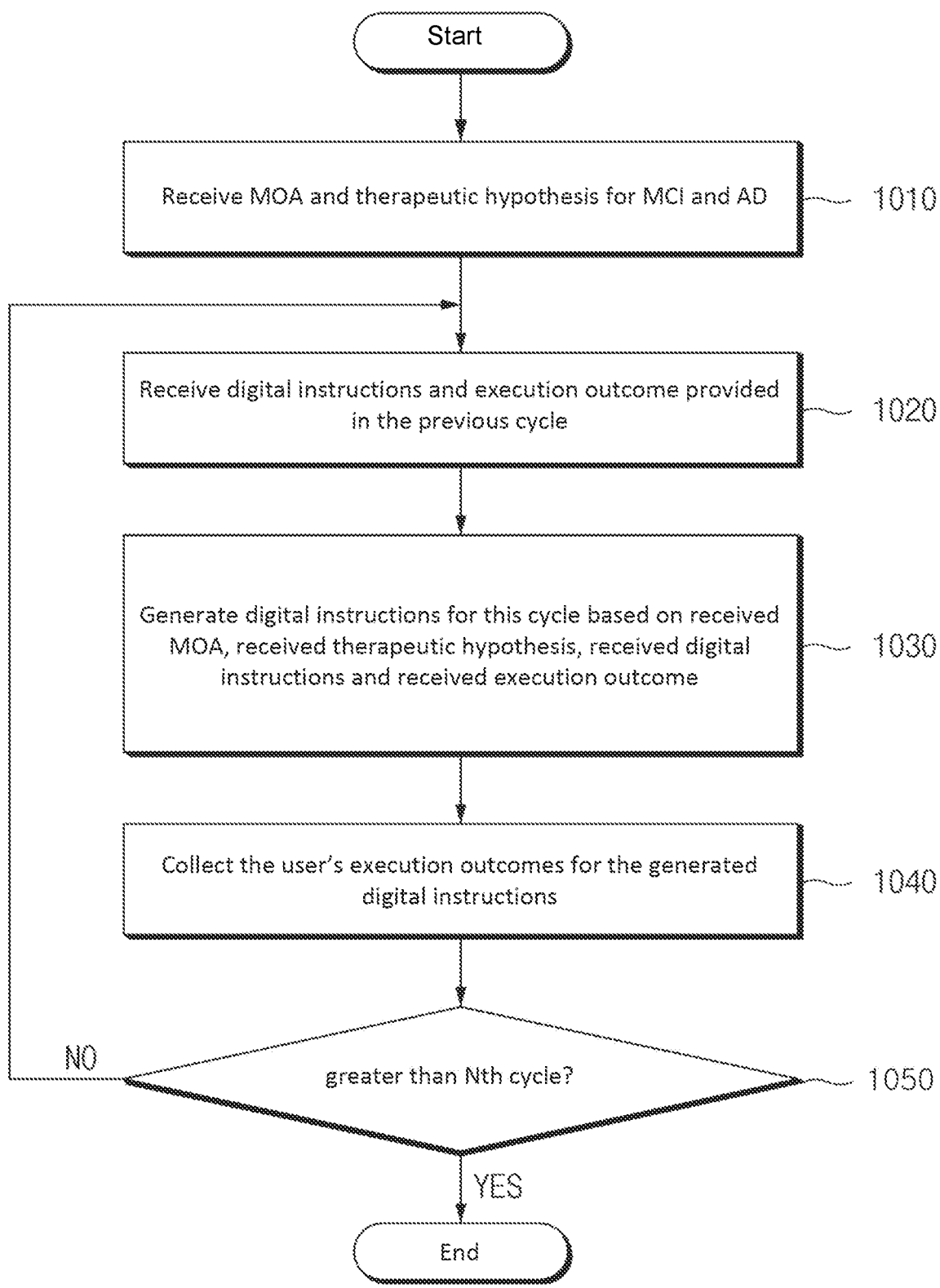
FIG. 10 is a diagram illustrating an example procedure that repeats the execution of digital instructions based on feedback for treating or inhibiting progression of MCI and AD.

FIG. 10 is a diagram illustrating an example procedure that repeats the execution of digital instructions based on feedback for treating or inhibiting progression of MCI and AD, which may be used in combination with any of other embodiments described herein.

In FIG. 10, it is explained that generation of the digital instructions and collection of the execution outcomes at the digital application for treating MCI and AD are executed multiple times (e.g., N times). In this case, at step 1010, the MOA and the therapeutic hypothesis for MCI and AD may be input first. Also, at step 1020, the digital instructions provided in the previous cycle and the execution outcome data may be received. When the first cycle of execution is now in progress, step 1020 may be omitted because there are no previous data.

At step 1030, digital instructions for this cycle may be generated based on the input MOA and therapeutic hypothesis, the digital instruction provided in the previous cycle, and the execution outcome data. At step 1040, the user's execution outcomes of the generated digital instructions may be collected.

At step 1050, it is determined whether this cycle is greater than $N^{th}$ cycle. If this cycle is less than the $N^{th}$ cycle (i.e. NO), this may return again to step 1020, thus repeatedly executing step 1020 to step 1040. On the other hand, if this cycle is greater than the $N^{th}$ cycle (i.e. YES), that is, when the generation of the digital instructions and the collection of the execution outcomes are executed N times, a feedback operation may be terminated. The number N may be pre-configured, predetermined or determined by a medical professional depending on the status of the patient.

Figure 11:
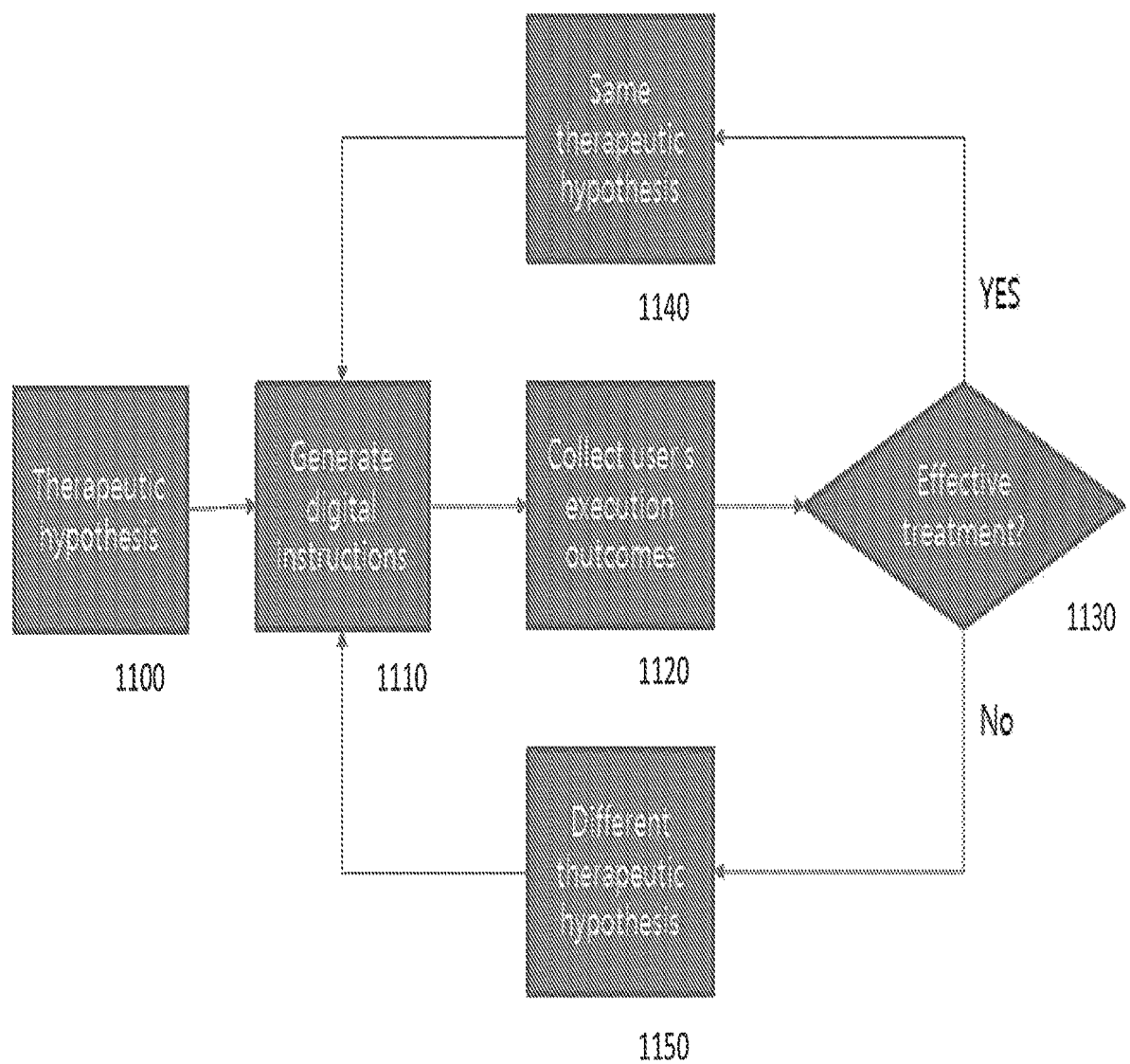
FIG. 11 is a diagram illustrating another example procedure that repeats the execution of digital instructions based on feedback for treating or inhibiting progression of MCI and AD.

FIG. 11 is a diagram illustrating another example procedure that repeats the execution of digital instructions based on feedback for treating or inhibiting progression of MCI and AD, which may be used in combination with any of other embodiments described herein.

Referring to FIG. 11, it is explained that generation of the digital instructions and collection of the execution outcomes at the application for treating MCI and AD are executed repeatedly. For example, at step 1110, the digital instructions may be generated if MOA and therapeutic hypothesis of MCI and AD are entered at step 1100. If the first cycle of execution is in progress, the first therapeutic hypothesis is input as 0(e.g., TH 0) at step 1100. Also, at step 1120, the execution outcome data of the digital action instructions of the current cycle can be collected.

At step 1130, whether the current cycle has had sufficient therapeutic effect may be determined. If considered sufficient, the same therapeutic hypothesis is input for the next cycle at step 1140. If not, new therapeutic hypothesis may be generated based on the action instructions and execution outcomes of the current cycle at step 1150.

The algorithm above illustrates the feed process per cycle to attain optimal action instructions and execution outcomes from patients based on the MCI and AD therapeutic hypothesis which helps conclude optimal therapeutic effect for each patient.

The determination at step 1130 may be made by the doctor who monitors the digital instructions and execution outcomes. However, not all instruction-execution cycles need for the determination. Doctors can make judgments by collecting and analyzing the execution outcomes for different action instructions regularly such as on a pre-doctor-designated period basis, daily basis, weekly basis and monthly basis.

Step 1150 to step 1110 shows the process of creating a new therapeutic hypothesis to generate optimal action instructions for patient treatment. As described in FIGS. 5A and 5B, using the "neuro-humoral factor-imaginary parameter-module" interrelation, at step 1150 a new weight of neuro-humoral factors may be generated based on the new therapeutic hypothesis. The changes in the weight may be converted to the weight for each module of the DTx modules at step 1110. For example, through the feedback loop of step 1150—step 1110, combination for each module, repeat per module, execute time, intensity and others can be optimized.

Figure 12:
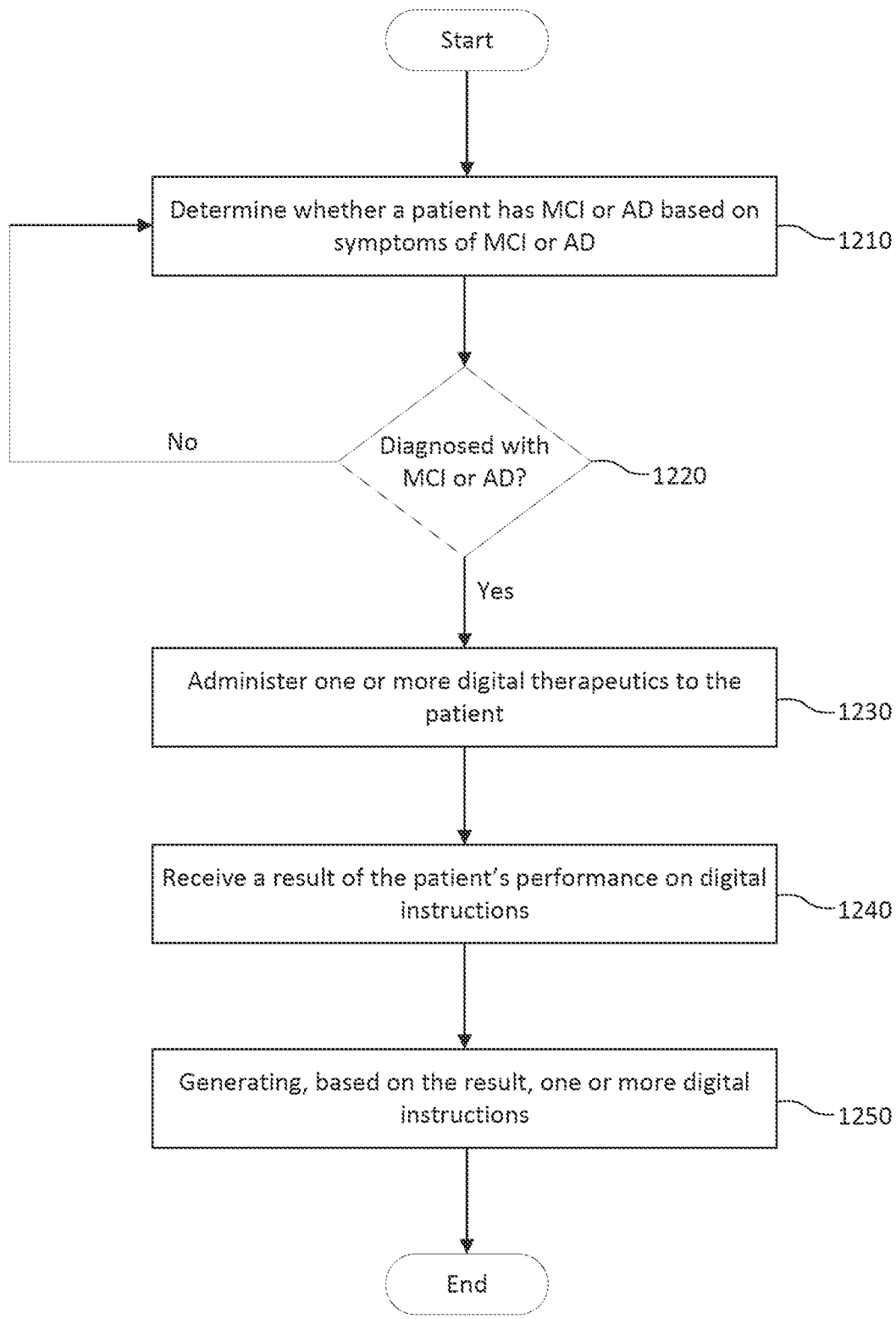
FIG. 12 is a diagram illustrating an example procedure for treating a patient with MCI or dementia by digital therapeutics.

FIG. 12 is a diagram illustrating an example procedure for treating a patient with MCI or dementia by digital therapeutics, which may be used in combination with any of other embodiments described herein. As illustrated in FIG. 12, at step 1210, a medical professional (e.g., doctor) may determine determining whether the patient has MCI or dementia based on one or more symptoms of the MCI or the dementia. If the patient is diagnosed with MCI or dementia at step 1220, the medical professional may prescribe or administer one or more digital therapeutics to the patient to improve the patient's neurohumoral factors that caused the MCI or the dementia of the patient. The neurohumoral factors may include, but are not limited to, sex steroid hormone, insulin-like growth factor-2 (IGF-2), β-catenin in Wnt signaling, Bcl-2—associated athanogene 1 (BAG1), cAMP response element-binding protein (CREB), inflammation factors, corticosteroids, or neurohormones. More specifically, the corticosteroids may include cortisol and glucocorticoid, and the neurohormones may include dopamine, noradrenaline, and somatostatin.

The digital therapeutics prescribed or administered by the medical professional may comprise one or more digital instructions that are generated to treat imbalance of the neurohumoral factors based on the neurohumoral change among the neurohumoral factors. The neurohumoral imbalance (i.e. the imbalance of the neurohumoral factors) that may have caused the MCI or dementia to the patient may include, but are not limited to, a sex steroid hormone imbalance, a IGF-2 decrease, a β-catenin degradation, a BAG1 inactivation, a CREB inactivation, an increase in inflammation factors, a corticosteroids increase, or a neurohormone decrease.

The patient may perform the one or more digital instructions, thereby improving their neurohumoral imbalance. Examples of the digital instructions may include, but are not limited to, an execution environment setting, a lifestyle change, learning, exercising, being affirmative or an achievement task. The neurohumoral change caused by the patient's execution of the digital instructions may include, but are not limited to, neurogenesis in the patient's hippocampus, anti-inflammation, anti-stress, or anti-depression. Particularly, among the digital instructions, at least one of the execution environment setting, the lifestyle change, or the learning may be associated with the neurogenesis in the patient's hippocampus to treat at least one of the sex steroid hormone imbalance, the IGF-2 decrease, the β-catenin degradation, the BAG1 inactivation, or the CREB inactivation. Among the digital instructions, at least one of the execution environment setting or the learning may be associated with the anti-stress to treat the corticosteroids increase. Among the digital instructions, exercising may be associated with the anti-inflammation to treat the increase in inflammation factors. Among the digital instructions, the at least one of the execution environment setting, the being affirmative or the achievement task may be associated with the anti-depression to treat the neurohormone decrease.

At step 1240, the medical professional may receive or monitor the result of the patient's performance of the one or more digital instructions. The patient's performance of the one or more digital instructions may be repeated predetermined multiple times to improve the neurohumoral imbalance. After receiving or monitoring the patient's performance, at step 1250, different. or the same digital instructions may be generated by the device or under the supervision of the medical professional. These digital instructions generated based on the result of the patient's performance may be used to treat imbalance of the plurality of neurohumoral factors.

In one embodiment, a patient may directly use a user device or apparatus to treat the patient's MCI or dementia.

For example, the device may generate one or more digital therapeutics to improve the patient's neurohumoral factors that has caused the MCI or dementia. The digital therapeutics may comprise one or more digital instructions that are generated to treat at least one imbalance of the neurohumoral factors based on at least one neurohumoral change among the neurohumoral factors by the patient's performance of the one or more digital instructions. The device may also be configured to generate, based on the patient's performance of the one or more digital instructions, different or the same digital instructions to treat at least one imbalance of the neurohumoral factors of the patient.

The device may communicate with other devices (e.g., server) to report the result of the patient's performance on the one or more digital instructions. For example, the device used by the patient may transmit the result of patient's performance on the digital instructions to the server for the medical institution (e.g., hospital) or the device used by the medical professional. The device used by the patient may also receive, from other devices (e.g., server) second digital instructions. These second digital instructions may be the same or different digital instructions that the patient performed and reported. The second digital instructions may be instructed by the medical professional or the device used by the medical institution.

Figure 13:
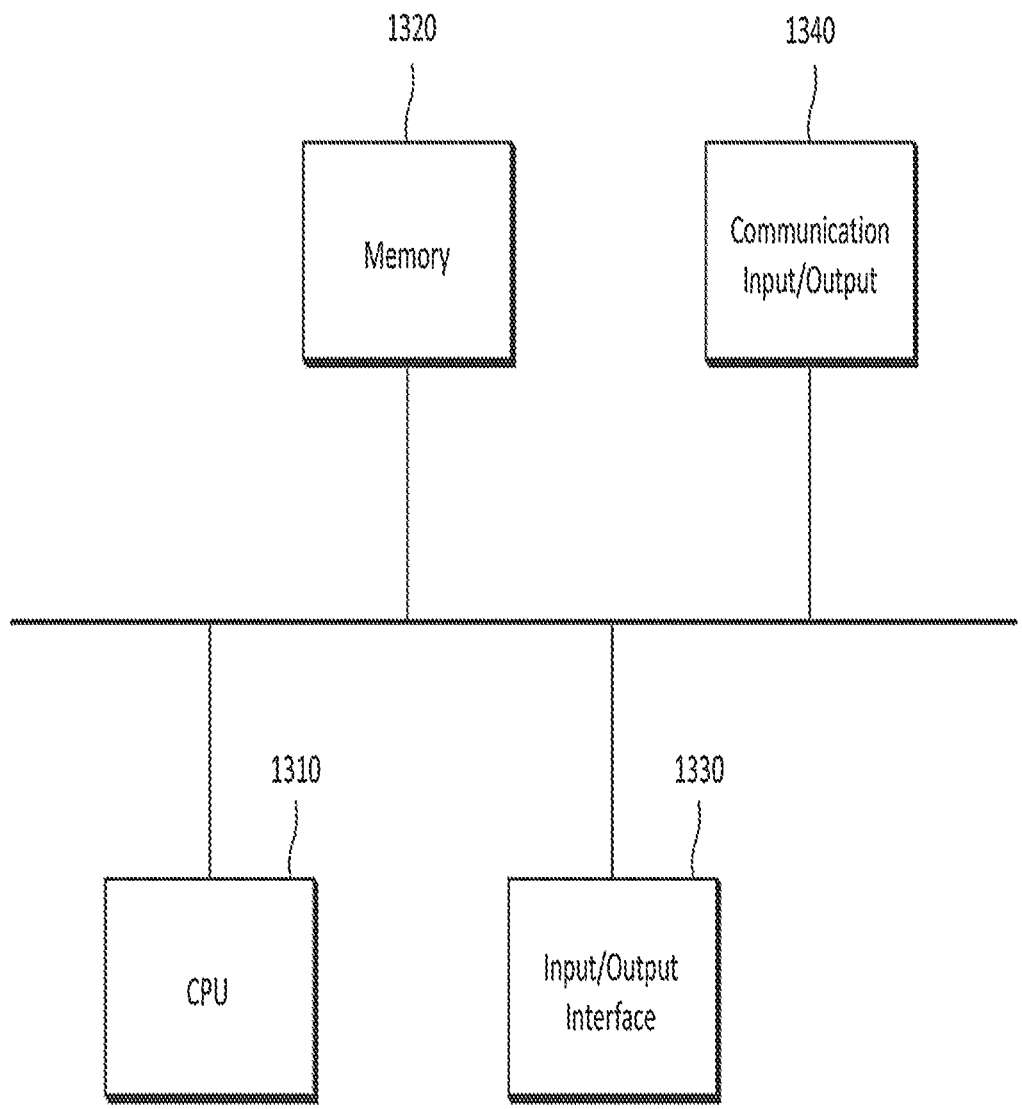
FIG. 13 is a diagram illustrating an example hardware configuration of a user device for treating or inhibiting progression of MCI and AD.

FIG. 13 is a diagram illustrating an example hardware configuration of a user device for treating or inhibiting progression of MCI and AD, which may be used in combination with any of other embodiments described herein.

Referring to FIG. 13, hardware of the digital apparatus for treating MCI and AD may include a CPU 1310, a memory 1320, an input/output I/F 1330, and a communication I/F 1340.

The CPU 1310 may be a processor configured to execute a digital program for treating MCI and AD stored in the memory 1320, process various data for treating digital MCI and AD, and execute functions associated with the digital therapy for MCI and AD. That is, the CPU 1310 may act to execute functions for each of the configurations by executing the digital program for treating MCI and AD stored in the memory 1320.

The memory 1320 can have a digital program for treating MCI and AD stored therein. Also, the memory 1320 may include the data used for the digital therapy for MCI and AD included in database, for example, the patient's digital instructions, instruction execution outcomes, the patient's medical information, and the like.

The memory 1320 may be a volatile memory or a nonvolatile memory. If the memory 1320 is a volatile memory, RAM, DRAM, SRAM, and the like may be used as the memory 1320. If the memory 1320 is a nonvolatile memory, ROM, PROM, EAROM, EPROM, EEPROM, a flash memory, and the like may be used as the memory 620. Examples of the memories 1320 as listed above are given by way of illustration only, and are not intended to limit the present invention.

The input/output I/F 1330 can provide an interface in which input apparatuses(not shown) such as a keyboard, a mouse, a touch panel, and the like, and output apparatuses such as a display(not shown), and the like may be connected to the CPU 1310 to transmit and receive data.

The communication I/F 1340 is configured to transmit and receive various types of data to/from a server or other user device, and may be one of various apparatuses capable of supporting wire or wireless communication. For example, the types of data on the aforementioned digital behavior-based therapy may be received from a separately available external server through the communication I/F 1340.

As described above, the digital instructions generated to treat MCI and/or AD may be recorded in the memory 1320 and processed at the CPU 1310, for example, so that the digital instructions can be realized as a module configured to execute each of functional blocks.

Although all the components of the embodiment of the present invention are described to be combined and operated together, the invention is not necessarily limited to the embodiment of present invention. That is, within the scope of the purpose of the invention, the components can be selectively combined and operated.

The terms "comprises," "comprising," "includes" and/or "including," used above, specify the presence of stated features, integers, steps, operations, elements, components and/or groups thereof, but do not preclude the presence or addition of one or more other features, integers, steps, operations, elements, components and/or groups thereof. All terminologies used herein including technical and scientific terminologies may hold the same meaning as are generally understood by those skilled in the art of technology of the present invention. Predefined, commonly used terminologies can hold the same or similar meaning to the contextual meaning of the relevant technology, and is not interpreted in an ideal or overly formal sense unless the context clearly indicates otherwise.

While the invention has been shown and described with reference to certain exemplary embodiments thereof, it will be understood by those skilled in the art that various changes in form and details may be made therein without departing from the spirit and scope of the invention as defined by the appended claims. In other words, the embodiments disclosed in the present invention are not intended to limit but rather to illustrate, and the exemplary embodiments do not limit the scope of the technical ideas of the invention. The scope of protection of the invention should be construed in accordance with the following claims, and all technical ideas within the same scope should be construed as being within the scope of the rights of this invention.

Although features and elements are described above in particular combinations, one of ordinary skill in the art will appreciate that each feature or element can be used alone or in any combination with the other features and elements. In addition, the methods described herein may be implemented in a computer program, software, or firmware incorporated in a computer-readable medium for execution by a computer or processor. Examples of computer-readable media include electronic signals (transmitted over wired or wireless connections) and computer-readable storage media. Examples of computer-readable storage media include, but are not limited to, a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs). A processor in association with software may be used to implement a radio frequency transceiver for use in a WTRU, UE, terminal, base station, RNC, or any host computer.

The present disclosure includes the following embodiments.

Embodiment 1. A method of treating a patient with mild cognitive impairment (MCI) or dementia by one or more digital therapeutics, the method comprising: administering the one or more digital therapeutics to the patient to improve a plurality of neurohumoral factors that cause the MCI or the dementia of the patient, wherein the one or more digital therapeutics comprise an instruction for an achievement task, detecting at least one neurohumoral change among the plurality of neurohumoral factors occurring because of the patient's performance of the one or more digital instructions, detecting the patient's adherence to the one or more digital instructions by at least one sensor selected from the group consisting of a gyroscope, an accelerometer, a hall effect sensor, a magnetometer, an orientation sensor, a proximity sensor, a temperature sensor, a time sensor, a geolocation sensor, an altimeter, a light sensor, a touch sensor, a magnetometer, a barometer, a gesture sensor, a biometric sensor, a humidity sensor, and generating one or more digital instructions to treat at least one imbalance of the plurality of neurohumoral factors based on the at least one neurohumoral change and the adherence.

Embodiment 2. The method of embodiment 1, wherein the plurality of neurohumoral factors includes at least one of sex steroid hormone, insulin-like growth factor-2 (IGF-2), β-catenin in Wnt signaling, Bcl-2—associated athanogene 1 (BAG1), cAMP response element-binding protein (CREB), inflammation factors, corticosteroids, or neurohormones.

Embodiment 3. The method of embodiment 2, wherein the corticosteroids include cortisol and glucocorticoid, and wherein the neurohormones include dopamine, noradrenaline, and somatostatin.

Embodiment 4. The method of embodiment 1, wherein the one or more digital instructions further includes at least one instruction selected from the group consisting of instructions for an execution environment setting, a lifestyle change, learning, exercising, and being affirmative.

Embodiment 5. The method of embodiment 4, wherein the at least one imbalance of the plurality of neurohumoral factors includes at least one of a sex steroid hormone imbalance, an IGF-2 decrease, a β-catenin degradation, a BAG1 inactivation, a CREB inactivation, an increase in inflammation factors, a corticosteroids increase, or a neurohormone decrease.

Embodiment 6. The method of embodiment 5, wherein the at least one neurohumoral change in the patient includes at least one of neurogenesis in the patient's hippocampus, anti-inflammation, anti-stress, or anti-depression.

Embodiment 7. The method of embodiment 6, wherein the at least one instruction further comprises instructions for the execution environment setting, the lifestyle change, or the learning, and the at least one instruction is associated with the neurogenesis in the patient's hippocampus to treat at least one of the sex steroid hormone imbalance, the IGF-2 decrease, the β-catenin degradation, the BAG1 inactivation, or the CREB inactivation.

Embodiment 8. The method of embodiment 6, wherein the at least one instruction further comprises instructions for the execution environment setting or the learning, and the at least one instruction is associated with the anti-stress to treat the corticosteroids increase.

Embodiment 9. The method of embodiment 6, wherein the at least one instruction further comprises instructions for the exercising, and the exercising is associated with the anti-inflammation to treat the increase in inflammation factors.

Embodiment 10. The method of embodiment 6, wherein the at least one instruction further comprises instructions for the execution environment setting, or the being affirmative, and the at. least one instruction is associated with the anti-depression to treat the neurohormone decrease.

Embodiment 11. The method of embodiment 1, further comprising: receiving a result of the patient's performance of the one or more digital instructions that were repeated by the patient predetermined multiple times; and generating, based on the result, one or more digital instructions to treat at least. one imbalance of the plurality of neurohumoral factors.

Embodiment 12. The method of embodiment 1, wherein the one or more digital therapeutics is performed by a wireless transmit/receive unit (WTRU).

Embodiment 13. A method of treating a subject having mild cognitive impairment (MCI) or dementia by one or more digital therapeutics, the method comprising: administering, by the subject, the one or more digital therapeutics to improve a plurality of neurohumoral factors that cause the MCI or the dementia of the subject, wherein the one or more digital therapeutics comprise first one or more digital instructions that are generated to treat at least one imbalance of the plurality of neurohumoral factors based on at least one neurohumoral change among the plurality of neurohumoral factors by performing the one or more digital instructions, and the first one or more digital instructions include an instruction for an achievement task.

Embodiment 14. The method of embodiment 13, wherein the plurality of neurohumoral factors includes at least. one of sex steroid hormone, insulin-like growth factor-2 (IGF-2), β-catenin in Wnt signaling, Bcl-2—associated athanogene 1 (BAG1), cAMP response element-binding protein (CREB), inflammation factors, corticosteroids that include cortisol and glucocorticoid, or neurohormones that include dopamine, noradrenaline, and somatostatin.

Embodiment 15. The method of embodiment 13, wherein the first one or more digital instructions further includes at least one of an execution environment setting, a lifestyle change, learning, exercising, or being affirmative.

Embodiment 16. The method of embodiment 13, wherein the at least one imbalance of the plurality of neurohumoral factors includes at least one of a sex steroid hormone imbalance, a IGF-2 decrease, a β-catenin degradation, a BAG1 inactivation, a CREB inactivation, an increase in inflammation factors, a corticosteroids increase, or a neurohormone decrease, and wherein the at least one neurohumoral change in the subject includes at least one of neurogenesis in the patient's hippocampus, anti-inflammation, anti-stress or anti-depression.

Embodiment 17. The method of embodiment 13, further comprising: receiving, by the subject, based on a result of performing the first one or more digital instructions, a second one or more digital instructions; and performing, based on the result, the second one or more digital instructions to treat at least one imbalance of the plurality of neurohumoral factors.

Embodiment 18. An apparatus for use by a subject having mild cognitive impairment (MCI) or dementia, the apparatus comprising: a processor configured to generate one or more digital therapeutics to improve a plurality of neurohumoral factors that cause the MCI or the dementia of the subject, wherein the one or more digital therapeutics comprise one or more digital instructions that are generated to treat at least one imbalance of the plurality of neurohumoral factors based on at least one neurohumoral change among the plurality of neurohumoral factors by the subject's performance of the one or more digital instructions.

Embodiment 19. The apparatus of embodiment 18, wherein the processor is further configured to generate, based on the subject's performance of the one or more digital instructions, second one or more digital instructions to treat at least one imbalance of the plurality of neurohumoral factors of the subject.

Embodiment 20. The apparatus of embodiment 18, further comprising: a transmitter configured to transmit, to another apparatus of a medical entity, a result of the subject's performance of the one or more digital instructions; and a receiver configured to receive, from the another apparatus, second one or more digital therapeutics that, includes second one or more digital instructions generated based on the result in order to treat at least one imbalance of the plurality of neurohumoral factors.

Embodiment 21. The method of embodiment 1, wherein the one or more digital instructions further comprise an instruction for an execution environment setting, the execution environment setting includes brightness, coziness, or comfort.

Embodiment 22. The method of embodiment 1, wherein the one or more digital instructions further comprise an instruction for a lifestyle change, the lifestyle change includes new experience, traveling, or sex hormone balance recovery.

Embodiment 23. The method of embodiment 1, wherein the one or more digital instructions further comprise an instruction for learning, the learning includes recollection learning, or memory recognition treatment.

Embodiment 24. The method of embodiment 1, wherein the one or more digital instructions further comprise an instruction for exercising, the exercising includes short-term acute exercise.

Embodiment 25. The method of embodiment 1, wherein the one or more digital instructions further comprise an instruction for an achievement task, the achievement task includes positive feelings, a project, a voluntary DTx participation.

Embodiment 26. The method of embodiment 1, wherein the one or more digital instructions further includes instructions for an execution environment setting, a lifestyle change, learning, exercising, and being affirmative.

What is claimed:

1. A method of treating a patient with mild cognitive impairment (MCI) or dementia by one or more digital therapeutics, the method comprising:
    providing one or more first digital instructions to the patient to improve one or more neurohumoral factors that cause the MCI or the dementia of the patient,
    detecting at least one neurohumoral change among the one or more neurohumoral factors occurring because of the patient's performance of the one or more first digital instructions,
    detecting the patient's adherence to the one or more first digital instructions using a sensor, and
    generating one or more second digital instructions to treat at least one imbalance of the one or more neurohumoral factors based on the at least one neurohumoral change and the adherence,
    wherein the one or more neurohumoral factors comprises at least one of sex steroid hormone, insulin-like growth factor-2 (IGF-2), β-catenin in Wnt signaling, Bcl-2—associated athanogene 1 (BAG1), cAMP response element-binding protein (CREB), inflammation factors, corticosteroids, or neurohormones.

2. The method according to claim 1, wherein the one or more first digital instructions comprise an instruction for an achievement task.

3. A method of treating a subject having mild cognitive impairment (MCI) or dementia by one or more digital therapeutics, the method comprising:
    providing one or more first digital instructions to a first user who is a subject to MCI or dementia treatment, based on at least part of a plurality of digital therapeutic modules configured to regulate one or more neurohumoral factors to treat MCI or dementia, each of the plurality of digital therapeutic modules comprising one or more first digital instructions for the first user to follow;
    collecting the first user's execution outcomes of the one or more first digital instructions using a sensor, wherein the one or more neurohumoral factors comprises at least one of sex steroid hormone, insulin-like growth factor-2 (IGF-2), β-catenin in Wnt signaling, Bcl-2—associated athanogene 1 (BAG1), cAMP response element-binding protein (CREB), inflammation factors, corticosteroids, or neurohormones; and
    providing one or more second digital instructions to regulate the one or more neurohumoral factors to treat the MCI or the dementia based on the first user's execution outcomes of the one or more first digital instructions.

4. A digital system for treating mild cognitive impairment (MCI) or dementia, the digital system comprising a processor configured to:
    provide one or more first digital instructions to a first user who is a subject to MCI or dementia treatment, based on at least part of a plurality of digital therapeutic modules configured to regulate one or more neurohumoral factors to treat MCI or dementia, each of the plurality of digital therapeutic modules comprising one or more first digital instructions for the first user to follow,
    collect the first user's execution outcomes of the one or more first digital instructions using a sensor, wherein the one or more neurohumoral factors comprises at least one of sex steroid hormone, insulin-like growth factor-2 (IGF-2), β-catenin in Wnt signaling, Bcl-2—associated athanogene 1 (BAG1), cAMP response element-binding protein (CREB), inflammation factors, corticosteroids, or neurohormones, and
    provide one or more second digital instructions to regulate the one or more neurohumoral factors to treat the MCI or the dementia based on the first user's execution outcomes of the one or more first digital instructions.

5. The digital system of claim 4,
    wherein the one or more neurohumoral factors comprise the neurohormones, and
    wherein the neurohormones comprise at least one of dopamine, noradrenaline, or somatostatin.

6. The digital system of claim 4, wherein the plurality of digital therapeutic modules comprises at least one of an execution environment setup module, a lifestyle module, a learning module, an exercise module, or a positive/achievement module.

7. The digital system of claim 6,
    wherein the plurality of digital therapeutic modules comprises the execution environment setup module, and
    wherein the execution environment setup module comprises one or more execution environment setup instructions for balancing steroid sex hormones, balancing wnt/b-catenin, promoting IGF2 secretion, promoting BAG1 secretion, promoting CREB secretion, promoting neurohormone secretion, and inhibiting corticosteroid secretion.

8. The digital system of claim 6, wherein the one or more execution environment setup instructions comprise at least one of digital instructions related to brightness environment setting, coziness setting, familiarity setting, application environment setting, or location setting for the first user.

9. The digital system of claim 6,
wherein the plurality of digital therapeutic modules comprises the lifestyle module, and
wherein the lifestyle module comprises one or more lifestyle instructions for balancing steroid sex hormones, balancing wnt/b-catenin, promoting IGF2 secretion, promoting BAG1 secretion, and promoting CREB secretion.

10. The digital system of claim 9,
wherein the one or more lifestyle instructions comprise at least one of digital instructions related to new experience, travel, balance of sex hormones, diet recording, or nutrition evaluation for the first user.

11. The digital system of claim 6,
wherein the plurality of digital therapeutic modules comprises the learning module, and
wherein the learning module comprises one or more learning instructions for balancing steroid sex hormones, balancing wnt/b-catenin, promoting IGF2 secretion, promoting BAG1 secretion, promoting CREB secretion, and inhibiting corticosteroid secretion.

12. The digital system of claim 11,
wherein the one or more learning instructions comprise at least one of digital instructions related to recollection learning or memory recognition treatment for the first user.

13. The digital system of claim 6,
wherein the plurality of digital therapeutic modules comprises the exercise module, and
wherein the exercise module comprises one or more exercise instructions for decreasing inflammation factors.

14. The digital system of claim 13, wherein the one or more exercise instructions comprise one or more digital instructions related to acute exercise for the first user during a predetermined time.

15. The digital system of claim 6,
wherein the plurality of digital therapeutic modules comprises the positive/achievement module, and
wherein the positive/achievement module comprises one or more positive/achievement instructions for promoting neurohormone secretion.

16. The digital system of claim 15,
wherein the one or more positive/achievement instructions comprise at least one of digital instructions related to positive emotion, task completion, project assignment, or voluntary participation encouragement for the first user.

17. The digital system of claim 4, wherein the plurality of digital therapeutic modules comprises that are deduced in relation to parameters about neurogenesis in hippocampus, anti-inflammation, anti-stress, or ant-depression.

18. The digital system of claim 17, wherein the plurality of digital therapeutic modules comprises digital instructions that are deduced based on physiological interrelation between the one or more neurohumoral factors to treat MCI or dementia and the parameters.

19. The digital system of claim 4,
wherein the one or more second digital instructions are provided to the first user based on at least part of a plurality of second digital therapeutic modules, each of the second digital therapeutic modules comprising one or more second digital instructions for the first user to follow, and
wherein the one or more second digital instructions are different from the one or more first digital instructions.

20. The digital system of claim 19, wherein the processor is further configured to:
transmit the first user's execution outcomes of the one or more first digital instructions to a server, and
receive the one or more second digital instructions from the server based on the first user's execution outcomes of the one or more first digital instructions.

21. The digital system of claim 4, wherein the processor is further configured to generate the one or more digital instructions based on at least one of information received from the first user or input from a second user.

22. The digital system of claim 21, wherein the input from a second user comprises an outcome of the second user's prescription for the first user.

23. The digital system of claim 21,
wherein the information received from the first user comprises at least one of the first user's basal factors, medical information, or digital therapeutics literacy;
wherein the basal factors comprise the first user's amount of activity, heart rates, sleep, and meals;
wherein the medical information comprises the first user's electronic medical record (EMR), family history, genetic vulnerability, and genetic susceptibility; and
wherein the digital therapeutics literacy comprises the first user's accessibility and an acceptance posture to the digital therapy and the apparatus.

* * * * *